US012649907B2

(12) United States Patent (10) Patent No.: US 12,649,907 B2
Perell et al. (45) Date of Patent: Jun. 9, 2026

(54) ALTERNATE DETERGENTS FOR VIRAL INACTIVATION

(71) Applicant: AMGEN INC., Thousand Oaks, CA (US)

(72) Inventors: Gabriella Perell, Thousand Oaks, CA (US); Rosa Daneshvar, Thousand Oaks, CA (US); Martina Kopp, Thousand Oaks, CA (US)

(73) Assignees: AMGEN INC., Thousand Oaks, CA (US); Avantor Performance Materials, LLC, Radnor, PA (US)

( * ) Notice: Subject to any disclaimer, the term of this patent is extended or adjusted under 35 U.S.C. 154(b) by 883 days.

(21) Appl. No.: 17/432,156

(22) PCT Filed: Mar. 18, 2020

(86) PCT No.: PCT/US2020/023245
§ 371 (c)(1),
(2) Date: Aug. 19, 2021

(87) PCT Pub. No.: WO2020/190985
PCT Pub. Date: Sep. 24, 2020

(65) Prior Publication Data
US 2022/0106573 A1 Apr. 7, 2022

Related U.S. Application Data

(60) Provisional application No. 62/820,330, filed on Mar. 19, 2019.

(51) Int. Cl.
| | |
|---|---|
| *C12N 7/00* | (2006.01) |
| *C07K 1/16* | (2006.01) |
| *C07K 1/34* | (2006.01) |
| *C12P 21/00* | (2006.01) |

(52) U.S. Cl.
CPC ................. *C12N 7/00* (2013.01); *C07K 1/16* (2013.01); *C07K 1/34* (2013.01); *C12P 21/00* (2013.01); *C12N 2740/13063* (2013.01)

(58) Field of Classification Search
CPC .. C12P 21/00; C07K 1/14; C07K 1/16; C12N 7/00
USPC ...................................................... 435/69.1
See application file for complete search history.

(56) References Cited

U.S. PATENT DOCUMENTS

| | | | |
|---|---|---|---|
| 6,319,494 | B1 | 11/2001 | Capon et al. |
| 7,067,298 | B2 | 6/2006 | Latham et al. |
| 7,741,465 | B1 | 6/2010 | Eshhar et al. |
| 10,611,795 | B2 | 4/2020 | Fisher et al. |
| 2012/0015862 | A1 | 1/2012 | Travis et al. |
| 2015/0306223 | A1 | 10/2015 | Conley et al. |
| 2016/0333046 | A1 | 11/2016 | Fisher et al. |
| 2020/0032163 | A1 | 1/2020 | Bouchez et al. |

FOREIGN PATENT DOCUMENTS

| | | | |
|---|---|---|---|
| CA | 2228031 | A1 | 2/1997 |
| WO | 97/04815 | A1 | 2/1997 |
| WO | 02/28422 | A2 | 4/2002 |
| WO | 2004/090114 | A2 | 10/2004 |
| WO | 2012/082931 | A1 | 6/2012 |
| WO | 2015/073633 | A1 | 5/2015 |
| WO | 2018/060522 | A1 | 4/2018 |
| WO | 2019/121846 | A1 | 6/2019 |
| WO | 2021/118900 | A1 | 6/2021 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Nardello-Rataj et al., Aqueous solutions of didecyldimethylammonium chloride and octaethylene glycol monododecyl ether: Toward synergistic formulations against enveloped viruses, International Journal of Pharmaceutics, vol. 511, pp. 550-559 (2016).
Aranha, Virological safety of biopharmaceuticals, BioProcess International, 17-20 (2005).
Aranha, Current issues in assuring virological safety of biopharmaceuticals, BioProcess International, 10(3):12-17 (2012).
Bosley et al., A method of HIV-1 inactivation compatible with antibody-based depletion of abundant proteins from plasma, Proteomics: Clin. Appl., 2(6):904-907 (2008).
Conley et al., Evaluation of eco-friendly zwitterionic detergents for enveloped virus inactivation, Biotechnology and Bioengineering, 114(4):813-820 (2017).
Durno et al., Viral inactivation: Low pH and detergent, PDA Journal of Pharmaceutical Science and Technology, 69(1):163-172 (2015).
Edwards et al., Solubilization of lecithin vesicles by C12E8: Structural transitions and temperature effects, Journal of Colloid and Interface Science, 147(1):1-21 (1991).
Eshhar et al., Tumor-specific T-bodies: towards clinical application, Cancer Immunol Immunotherapy, 45:131-136 (1997).
Hellstern et al., The use of solvent/detergent treatment in pathogen reduction of plasma, Transfusion Medicine and Hemotherapy, 38(1):65-70 (2011).
International Application No. PCT/US20/23245, International Preliminary Report on Patentability, mailed Sep. 30, 2021.
International Application No. PCT/US20/23245, International Search Report and Written Opinion, mailed Jun. 22, 2020.
Kaufman, Large Scale Mammalian Cell Culture, Marcel Dekker, New York, New York, 15-69 (1990).

(Continued)

*Primary Examiner* — Tekchand Saidha

*Assistant Examiner* — Mohammad Y Meah

(74) *Attorney, Agent, or Firm* — Hoffmann & Baron LLP

(57) ABSTRACT

Detergents for use to inactivate enveloped viruses, including detergents that are considered eco-friendly that can be used in biomanufacturing operations.

23 Claims, 13 Drawing Sheets

(56) References Cited

OTHER PUBLICATIONS

Kragh-Hansen et al., The mechanism of detergent solubilization of liposomes and protein-containing membranes, Biophysical Journal, 75(6):2932-2946 (1998).

Laws et al., Estrogenic activity of octylphenol, nonylphenol, bisphenol A and methoxychlor in rats, Toxicological Sciences, 54(1):154-167 (2000).

Liumbruno et al., Solvent/detergent plasma: pharmaceutical characteristics and clinical experience, Journal of Thrombosis and Thrombolysis, 39(1):118-128 (2015).

Remington, Fundamental strategies for viral clearance part 2: Technical approaches, BioProcess International, 13(5):10-17 (2015).

Romanowski et al., Variables affecting titer and long-term stability of virus stocks, BioProcess International, 44-52 (2008).

Sambrook et al. Molecular Cloning: A Laboratory Manual, 3rd ed., Cold Spring Harbor Laboratory Press, Cold Spring Harbor, N.Y. (2001).

Sambrook et al., Molecular cloning: A laboratory manual, Cold Spring Laboratory Press, Cold Spring Harbor, N.Y. (1989).

Viral safety evaluation of biotechnology products derived from cell lines of human or animal origin, Harmonization, I. C. O., Ed., Q5A (1999).

* cited by examiner

FIG. 1

Cymal

Anapoe

Fos-Choline

Thioglucoside

MAB #2, 5°C

MAB #2, 25°C

FUSION #2, 5°C

FUSION #2, 25°C

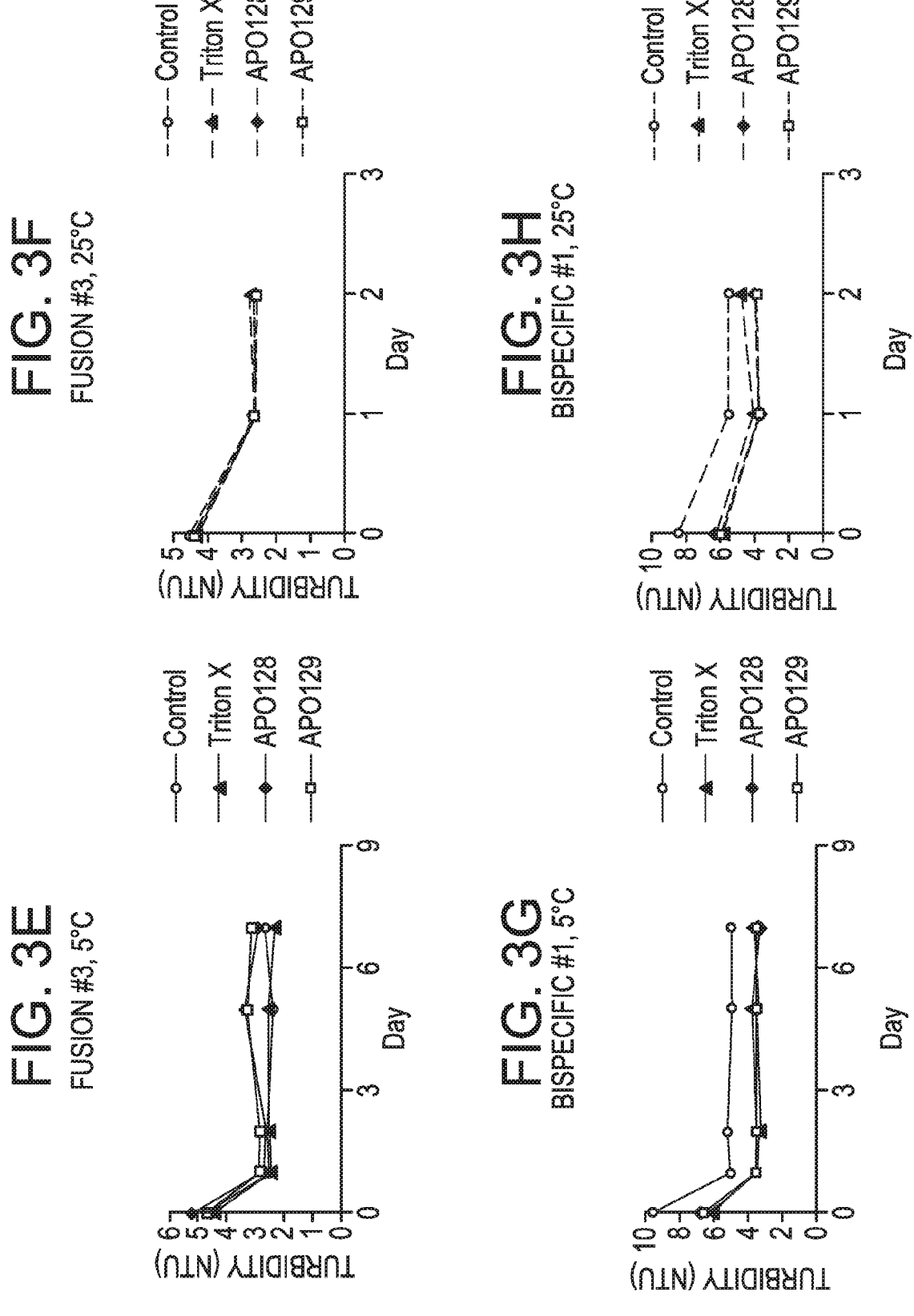

BITE #1, 5°C

BITE #1, 25°C

BITE #2, 5°C

BITE #2, 25°C

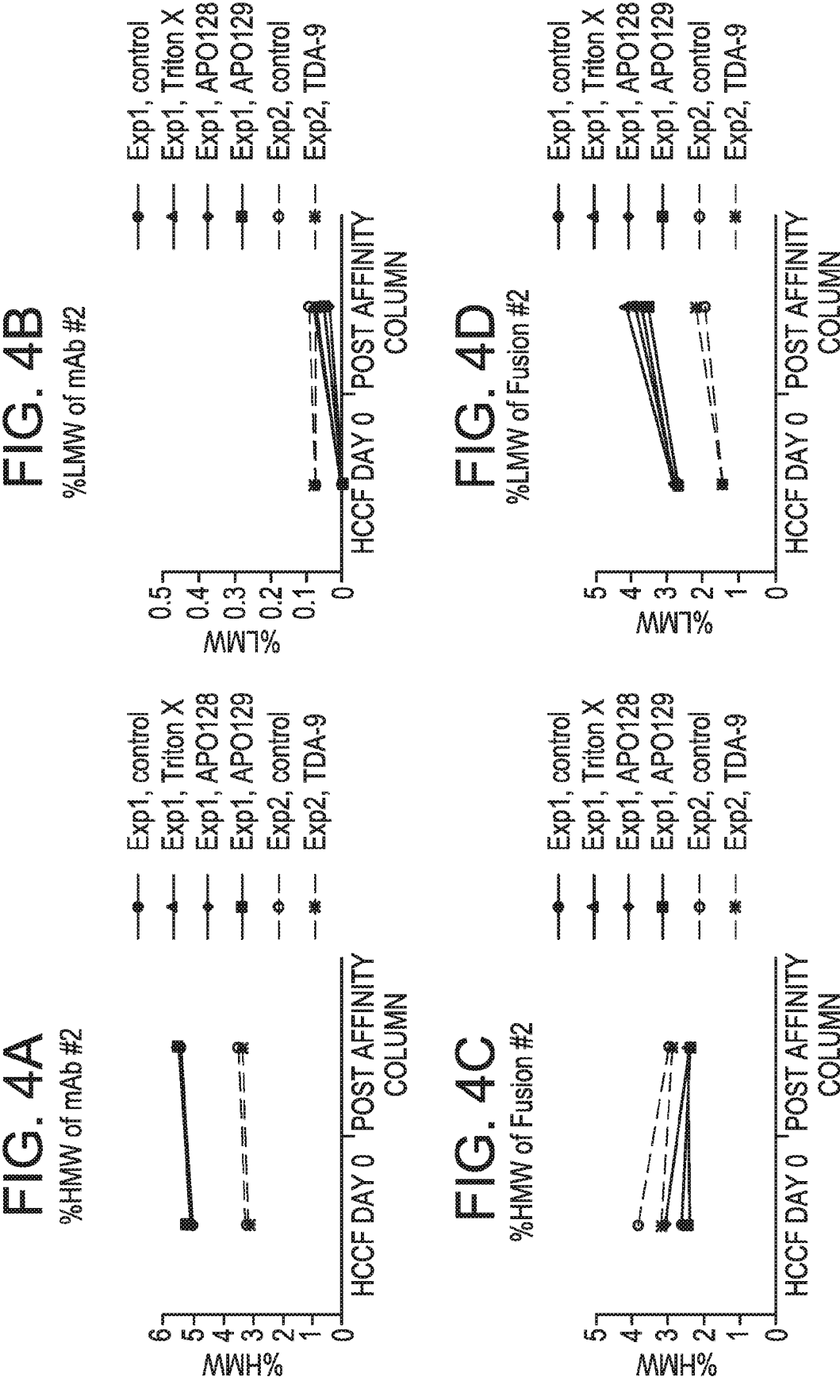

%LMW of Fusion #3

% LMW of Bispecific #1

%HMW of Fusion #3

% HMW of Bispecific #1

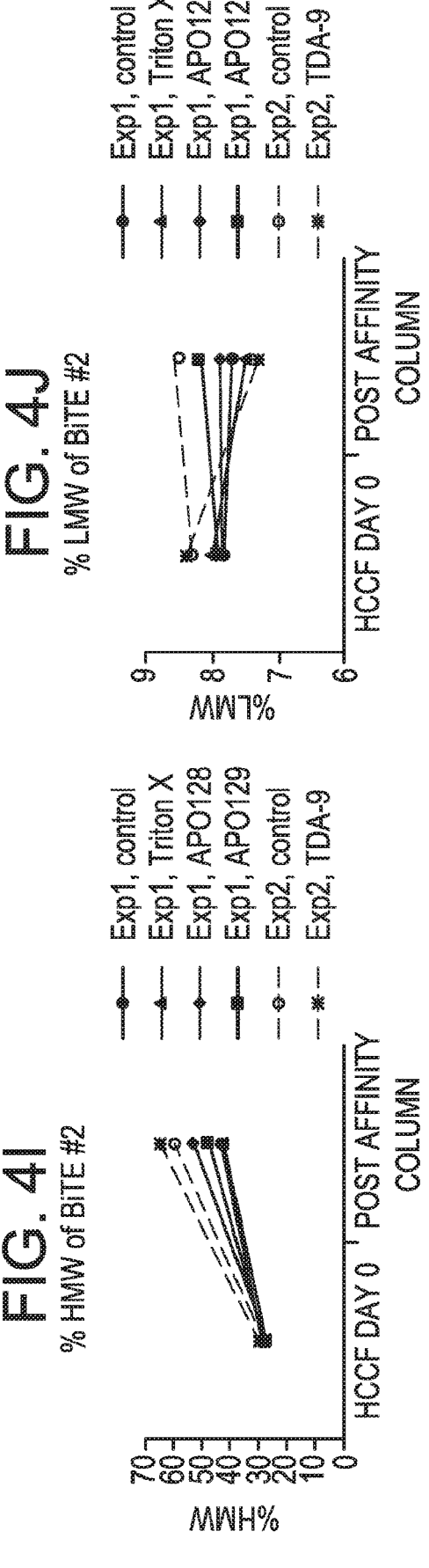

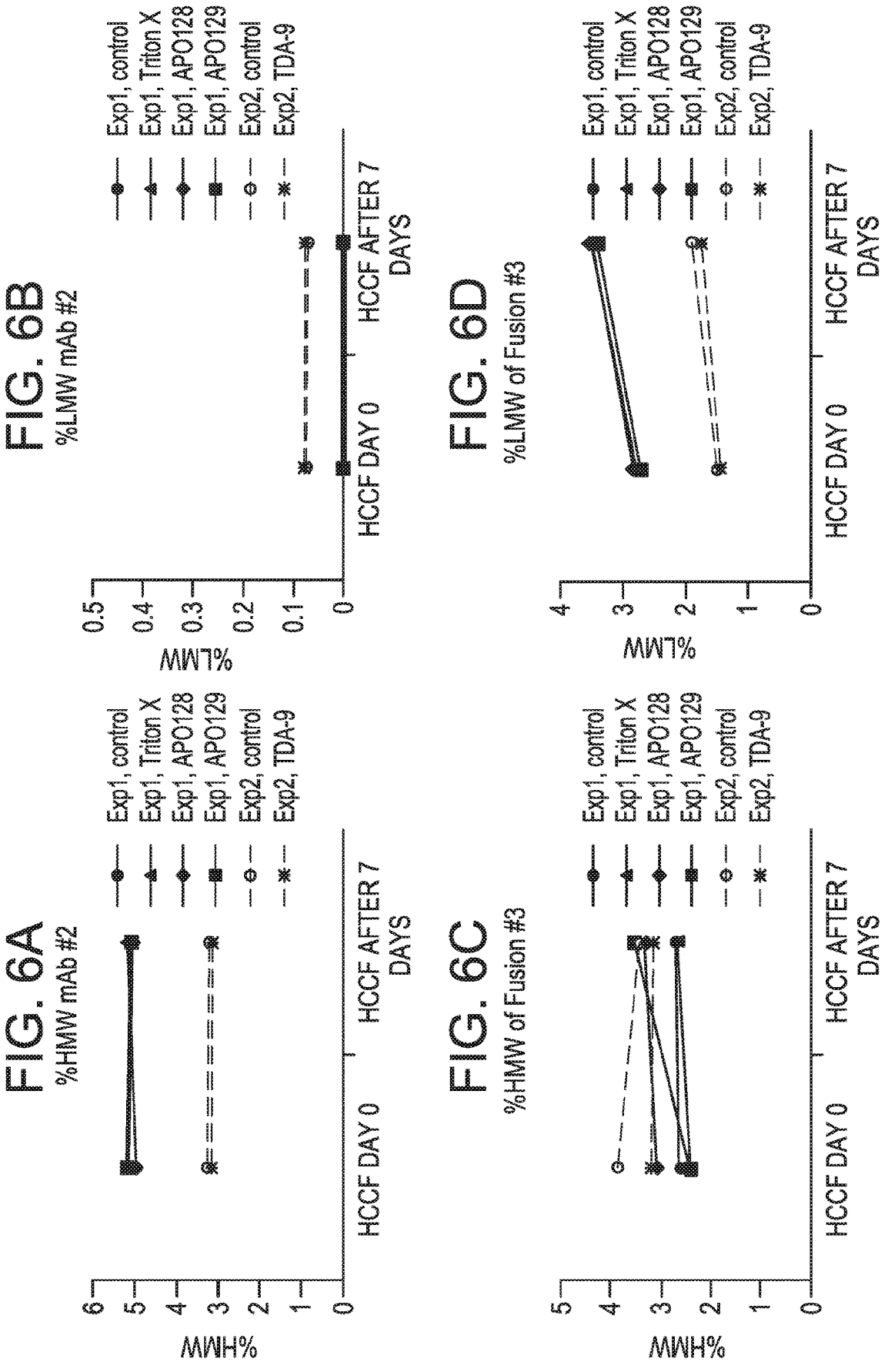

%HMW of Fusion #3

%LMW of Fusion #3

%HMW of Bispecific #1

%LMW of Bispecific #1

%LMW of BITE #2

%HMW of BITE #2

ALTERNATE DETERGENTS FOR VIRAL INACTIVATION

This application claims the benefit of U.S. Provisional Application No. 62/820,330, filed Mar. 19, 2019, which is hereby incorporated by reference.

FIELD OF DISCLOSURE

Detergents for use to inactivate enveloped viruses, including detergents those that are considered eco-friendly that can be used as alternatives to Triton X100 in biomanufacturing operations.

BACKGROUND

Viral inactivating process steps are critical to ensure the safety of protein therapeutics (Aranha, BioProcess International 2005; 17-20; Remington, Bioprocess International 2015, 13 (5), 10-17). Viral contaminants can arise from a variety of sources including media, manufacturing sites, or adventitious viral contaminants in Chinese Hamster Ovary (CHO) cell lines (Aranha, Bioprocess International 2012, 10 (3), 12-17). To ensure patient safety, biomanufacturers follow the guidelines identified by ICH-Q5A, which includes orthogonal viral clearance steps, including inactivation and filtration processes (Viral Safety Evaluation of Biotechnology Products Derived from Cell Lines of Human or Animal Origin. Harmonization, I. C. O., Ed. 1999; Vol. Q5A). Triton X-100 (polyoxyethylene octyl phenol ether) has long been used as an inactivating detergent that renders enveloped viruses inactive (Durno, and Tounekti, PDA Journal of Pharmaceutical Science and Technology, 2015, 69 (1), 163-172; Standard Practice for Process Step to Inactivate Rodent Retrovirus with Triton X-100 Treatment, ASTM International. In E3042-16, ASTM, Ed. West Conshohocken, PA, 2016). Detergents solubilize the membrane lipids that create the outer envelope layer (Liumbruno and Franchini, Journal of Thrombosis and Thrombolysis 2015, 39 (1), 118-128), therefore, detergents will only inactivate enveloped viruses, and not non-enveloped viruses (Hellstern and Solheim, Transfusion medicine and hemotherapy, 2011, 38 (1), 65-70). While Triton X-100 robustly inactivates viruses, the detergent also is an environmental toxin. One impact is its harmful effect on the endocrine system of fish. Triton X-100 breaks down into octylphenol, which mimics the hormone estradiol, leading to alterations within the hormonal system (Laws et al., Toxicological Sciences, 2000, 54 (1), 154-167). The European Union will begin to disallow the use of Triton X-100 by biopharmaceutical companies by 2020, as stated within Article 57 of the REACH, Commission Regulation (EU) Annex XIV to Regulation (EC) No 1907/2006 of the European Parliament and of the Council concerning the Registration, Evaluation, Authorization and Restriction of Chemicals ('REACH'). Union, E., Ed. 2017), therefore, it is pertinent to identify robust viral inactivating alternative detergents that are eco-friendly. Recent work by Conley et al. has identified lauryldimethylamine N-oxide (LDAO), an eco-friendly zwitterionic detergent that can inactivate enveloped viruses. (Conley et al., Biotechnology and Bioengineering 2017, 114 (4), 813-820 and Published US Patent Application No. 20150306223. Published US Patent Application No. 20160333046 also identified a number of detergents that show robust viral clearance, as well as ecological safety.

As such, there is a need for detergents that are effective for inactivation of envelope viruses, particularly detergents that are considered eco-friendly, for use within viral clearance process steps in biomanufacturing. The invention described herein meets this need by identifying effective, viral inactivating detergents that could be incorporated into the biomanufacturing processes for multiple therapeutic modalities.

BRIEF SUMMARY OF THE INVENTION

The invention provides a method for inactivating envelope virus in a fluid known or suspected to contain at least one enveloped virus, comprising obtaining a fluid known or suspected to contain at least one enveloped virus; exposing the fluid to a detergent from Table 1; at a concentration and for a time sufficient to cause viral inactivation. In one embodiment, the detergent has a CAS registry number of CAS 3055-99-0, CAS 3055-98-9, CAS 9043-30-5, CAS 85618-20-8, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 69227-93-6, CAS 82494-09-5, CAS 253678-67-0, CAS 106402-05-5, or CAS 93911-12-7. In one embodiment the detergent is selected from CAS 3055-99-0, CAS 3055-98-9, CAS 9043-30-5, or CAS 85618-20-8. In one embodiment the fluid is exposed to the detergent for at least 30 seconds to at least 60 minutes or longer. In one embodiment the fluid is exposed to the detergent for at least 10 minutes. In one embodiment the fluid is exposed to the detergent for at least 30 minutes. In one embodiment the fluid is exposed to the detergent for at least 60 minutes or longer. In one embodiment the concentration of the detergent is at least 2.5× to at least 10× or higher of its Critical Micelle Concentration (CMC). In one embodiment the concentration of the detergent is at least 5× of its CMC. In a related embodiment the concentration of the detergent is at least 7.5× of its CMC. In another related embodiment the concentration of the detergent is at least 10× of its CMC. In one embodiment exposure of the fluid to the detergent occurs at a temperature of at least 5° C. to 22° C. In a related embodiment exposure of the fluid to the detergent occurs at a temperature of at least 5° C. In a related embodiment exposure of the fluid to the detergent occurs at a temperature of at least 15° C. In a related embodiment exposure of the fluid to the detergent occurs at a temperature of at least 20° C. In another embodiment inactivation is determined using a $TCID_{50}$ assay. In one embodiment the fluid comprises a recombinant protein of interest. In one embodiment the fluid is harvested host cell culture fluid. In one embodiment the fluid is from an effluent stream, eluate, pool, storage or hold from a unit operation comprising a harvest step, a filtration step or a chromatography step. In a related embodiment the fluid is eluate collected from depth filtration, affinity chromatography, ion exchange chromatography, multimodal chromatography, hydrophobic interaction chromatography or hydroxyapatite chromatography. In one related embodiment the fluid is a pool containing harvested cell culture fluid, eluate from depth filtration, eluate from affinity chromatography, eluate from ion exchange chromatography, eluate from multimodal chromatography, eluate from hydrophobic interaction chromatography or eluate from hydroxyapatite chromatography. In another related embodiment the affinity chromatography is Protein A, Protein G, Protein A/G, or Protein L chromatography. In one embodiment, the detergent concentration is 5× of its CMC and the time is at least 10 minutes.

The invention provides a method for inactivating enveloped viruses during purification of a recombinant protein of interest comprising obtaining a fluid comprising the recombinant protein of interest which is known or suspected to contain at least one virus; subjecting the fluid to at least one detergent, wherein the detergent has a CAS registry number of CAS 3055-99-0, CAS 3055-98-9, CAS 9043-30-5, CAS 85618-20-8, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 69227-93-6, CAS 82494-09-5, CAS 253678-67-0, CAS 106402-05-5, or CAS 93911-12-7 at a concentration and for a time sufficient to cause inactivation of enveloped viruses in the fluid; and subjecting the viral inactivated fluid to at least one unit operation which includes at least a filtration step or a chromatography step. In one embodiment the detergent is selected from CAS 3055-99-0, CAS 3055-98-9, CAS 9043-30-5, and CAS 85618-20-8. In one embodiment the fluid is exposed to the detergent for at least 30 seconds to at least 60 minutes or longer. In a related embodiment the fluid is exposed to the detergent for at least 10 minutes. In a related embodiment the fluid is exposed to the detergent for at least 30 minutes. In another related embodiment the fluid is exposed to the detergent for at least 60 minutes or longer. In another embodiment the concentration of the detergent is at least 2.5× to at least 10× or higher of its Critical Micelle Concentration (CMC). In a related embodiment the concentration of the detergent is at least 5× of its CMC. In a related embodiment the concentration of the detergent is at least 7.5× of its CMC. In another related embodiment the concentration of the detergent is at least 10× of its CMC. In a related embodiment exposure of the fluid to the detergent occurs at a temperature of at least 5° C. to 22° C. In a related embodiment exposure of the fluid to the detergent occurs at a temperature of at least 5° C. In a related embodiment exposure of the fluid to the detergent occurs at a temperature of at least 15° C. In another related embodiment exposure of the fluid to the detergent occurs at a temperature of at least 20° C. In another embodiment inactivation is determined using a $TCID_{50}$ assay. In another embodiment the fluid comprises a recombinant protein of interest. In another embodiment the fluid is harvested host cell culture fluid. In another embodiment the fluid is from an effluent stream, eluate, pool, storage or hold from a unit operation comprising a harvest step, a filtration step or a chromatography step. In another embodiment the fluid is eluate collected from depth filtration, affinity chromatography, ion exchange chromatography, multimodal chromatography, hydrophobic interaction chromatography or hydroxyapatite chromatography. In another embodiment the fluid is a pool containing harvested cell culture fluid, eluate from depth filtration, eluate from affinity chromatography, eluate from ion exchange chromatography, eluate from multimodal chromatography, eluate from hydrophobic interaction chromatography or eluate from hydroxyapatite chromatography. In a related embodiment the affinity chromatography is Protein A, Protein G, Protein A/G, or Protein L chromatography. In another embodiment the chromatography is selected from affinity chromatography, Protein A chromatography, ion exchange chromatography, anion exchange chromatography, cation exchange chromatography; hydrophobic interaction chromatography; mixed modal or multimodal chromatography, or hydroxyapatite chromatography. In another embodiment the fluid is harvested host cell culture fluid and the unit operation includes depth filtration. In another embodiment the fluid is harvested host cell culture fluid and the unit operation includes Protein A affinity chromatography. In another embodiment the fluid is Protein A eluant and the unit operation includes depth filtration. In another embodiment the unit operation includes depth filtration. In one embodiment the unit operation includes microfiltration. In one embodiment, the detergent concentration is 5× of its CMC and the time is at least 10 minutes.

The invention also provides a method for producing an isolated, purified, recombinant protein of interest comprising establishing a cell culture in a bioreactor with a host cell expressing a recombinant protein and culturing the cells to express the recombinant protein of interest; harvesting cell culture fluid containing the recombinant protein of interest; processing the fluid containing the recombinant protein of interest through at least two unit operations, wherein during at least one unit operation there is a step where the fluid containing the recombinant protein of interest is combined with a detergent having a CAS registry number of CAS 3055-99-0, CAS 3055-98-9, CAS 9043-30-5, CAS 85618-20-8, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 69227-93-6, CAS 82494-09-5, CAS 253678-67-0, CAS 106402-05-5, or CAS 93911-12-7, at a detergent concentration and for a time sufficient to cause inactivation of enveloped virus; and obtaining an isolated, purified, recombinant protein of interest. In one embodiment the detergent is selected from CAS 3055-99-0, CAS 3055-98-9, CAS 9043-30-5, and CAS 85618-20-8. In one embodiment the fluid is exposed to the detergent for at least 30 seconds to at least 60 minutes or longer. In a related embodiment the fluid is exposed to the detergent for at least 10 minutes. In a related embodiment the fluid is exposed to the detergent for at least 30 minutes. In another related embodiment the fluid is exposed to the detergent for at least 60 minutes or longer. In another embodiment the concentration of the detergent is at least 2.5× to at least 10× or higher of its Critical Micelle Concentration (CMC). In a related embodiment the concentration of the detergent is at least 5× of its CMC. In a related embodiment the concentration of the detergent is at least 7.5× of its CMC. In another related embodiment the concentration of the detergent is at least 10× of its CMC. In a related embodiment exposure of the fluid to the detergent occurs at a temperature of at least 5° C. to 22° C. In a related embodiment exposure of the fluid to the detergent occurs at a temperature of at least 5° C. In a related embodiment exposure of the fluid to the detergent occurs at a temperature of at least 15° C. In another related embodiment exposure of the fluid to the detergent occurs at a temperature of at least 20° C. In another embodiment inactivation is determined using a $TCID_{50}$ assay. In another embodiment at least one unit operation includes a capture chromatography step selected from affinity chromatography, ion exchange chromatography, anion exchange chromatography, cation exchange chromatography, multi-modal chromatography, hydrophobic interaction chromatography, and hydroxyapatite chromatography. In another embodiment at least one unit operation includes a polish chromatography step selected from ion exchange chromatography, anion exchange chromatography, cation exchange chromatography, multi-modal chromatography, hydrophobic interaction chromatography, and hydroxyapatite chromatography. In another embodiment at least one unit operation includes a step selected from virus filtration, depth filtration, and UF/DF. In another embodiment the unit operation including the viral inactivation step occurs prior to a unit operation which includes affinity chromatography. In another embodiment a unit operation including affinity chromatography occurs before the unit operation including the viral inactivation step. In one embodiment the unit operation including the viral inactivation step occurs prior to a unit operation which includes depth filtration. In one embodiment is provided an isolated, purified, recombinant protein of interest according the method described above. In one embodiment is provided a pharmaceutical composition comprising the isolated protein of interest according to the method described above. In one embodiment, the detergent concentration is 5× of its CMC and the time is at least 10 minutes.

The invention also provides a method for producing an isolated, purified, recombinant protein of interest comprising establishing a cell culture in a bioreactor with a host cell expressing a recombinant protein and culturing the cells to express the recombinant protein of interest; harvesting cell culture fluid containing the recombinant protein of interest; subjecting the harvested fluid containing the recombinant protein of interest to a detergent having a CAS registry number of CAS 3055-99-0, CAS 3055-98-9, CAS 9043-30-5, CAS 85618-20-8, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 69227-93-6, CAS 82494-09-5, CAS 253678-67-0, CAS 106402-05-5, or CAS 93911-12-7, at a detergent concentration and for a time sufficient to cause inactivation of enveloped virus; processing the viral inactivated fluid containing the recombinant protein of interest through at least two additional unit operations; and obtaining an isolated, purified, recombinant protein of interest. In one embodiment the detergent is selected from CAS 3055-99-0, CAS 3055-98-9, CAS 9043-30-5, and CAS 85618-20-8. In one embodiment the fluid is exposed to the detergent for at least 30 seconds to at least 60 minutes or longer. In a related embodiment the fluid is exposed to the detergent for at least 10 minutes. In a related embodiment the fluid is exposed to the detergent for at least 30 minutes. In another related embodiment the fluid is exposed to the detergent for at least 60 minutes or longer. In another embodiment the concentration of the detergent is at least 2.5× to at least 10× or higher of its Critical Micelle Concentration (CMC). In a related embodiment the concentration of the detergent is at least 5× of its CMC. In a related embodiment the concentration of the detergent is at least 7.5× of its CMC. In another related embodiment the concentration of the detergent is at least 10× of its CMC. In a related embodiment exposure of the fluid to the detergent occurs at a temperature of at least 5° C. to 22° C. In a related embodiment exposure of the fluid to the detergent occurs at a temperature of at least 5° C. In a related embodiment exposure of the fluid to the detergent occurs at a temperature of at least 15° C. In another related embodiment exposure of the fluid to the detergent occurs at a temperature of at least 20° C. In another embodiment inactivation is determined using a $TCID_{50}$ assay. In another embodiment at least one unit operation includes a capture chromatography step selected from affinity chromatography, ion exchange chromatography, anion exchange chromatography, cation exchange chromatography, multi-modal chromatography, hydrophobic interaction chromatography, and hydroxyapatite chromatography. In another embodiment at least one unit operation includes a polish chromatography step selected from ion exchange chromatography, anion exchange chromatography, cation exchange chromatography, multi-modal chromatography, hydrophobic interaction chromatography, and hydroxyapatite chromatography. In another embodiment at least one unit operation includes a step selected from virus filtration, depth filtration, and UF/DF. In another embodiment the unit operation including the viral inactivation step occurs prior to a unit operation which includes affinity chromatography. In another embodiment a unit operation including affinity chromatography occurs before the unit operation including the viral inactivation step. In one embodiment the unit operation including the viral inactivation step occurs prior to a unit operation which includes depth filtration. In one embodiment is provided an isolated, purified, recombinant protein of interest according the method described above. In one embodiment is provided a pharmaceutical composition comprising the isolated protein of interest according to the method described above. In one embodiment, the detergent concentration is 5× of its CMC and the time is at least 10 minutes.

The invention also provides an isolated, purified, recombinant protein of interest according to the methods described herein. The invention also provides a pharmaceutical composition comprising the isolated protein of interest according to the methods provided herein.

BRIEF DESCRIPTION OF THE DRAWINGS

Figure 1:
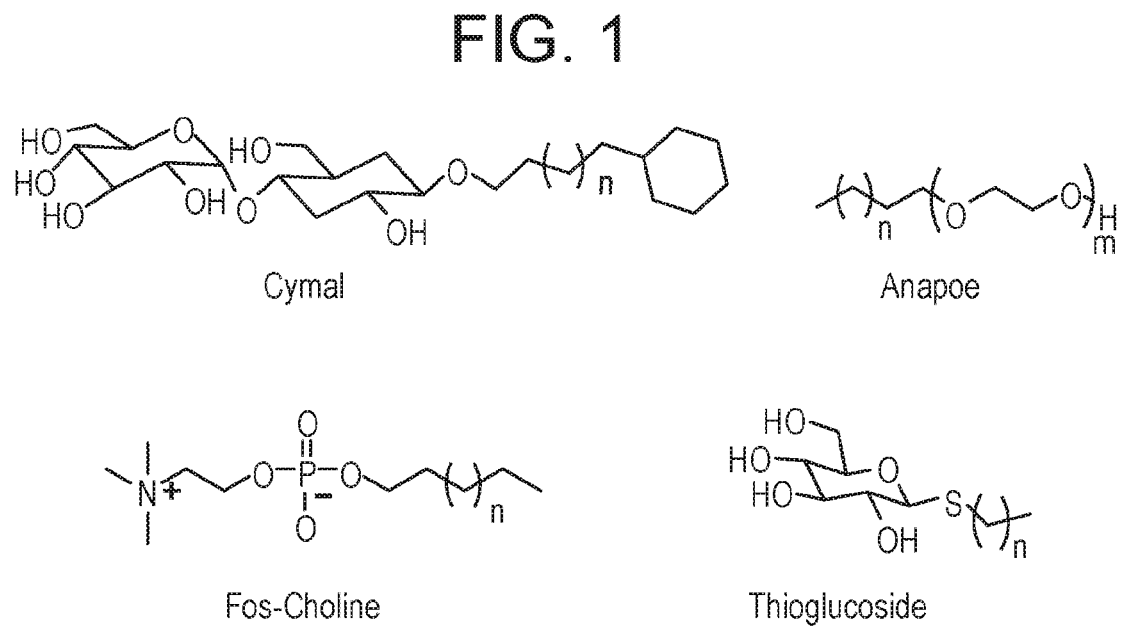

FIG. 1: Structurally different detergent classes identified to have viral inactivating properties.

DETAILED DESCRIPTION OF THE INVENTION

Figures 2A, 2B, 2C:
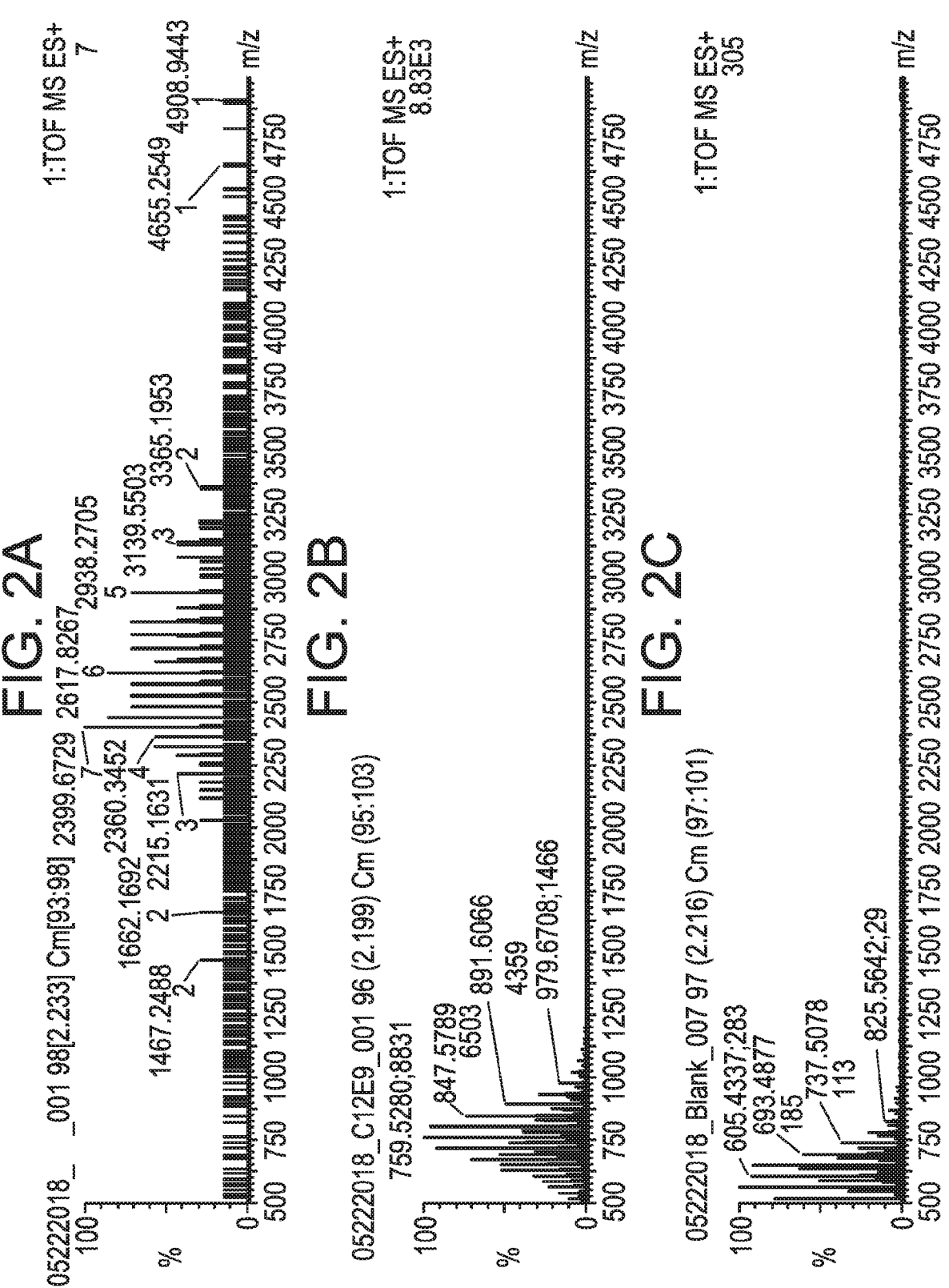
FIG. 2: Mass Spec Elution peaks for: A: mAb Elution after ProA purification. B: Blank run after detergent injection to verify clearance of detergent from detector. C: Spiked C12E9 detergent (0.03%) into water.
Figure 2D:
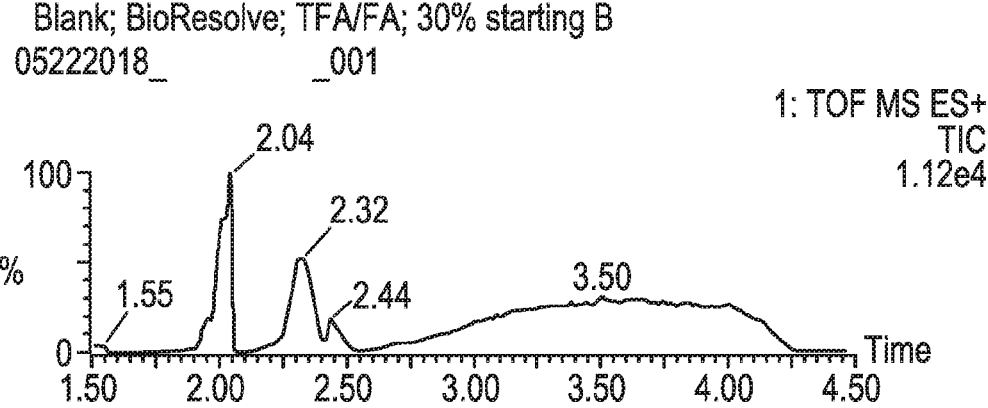
Figure 2E:
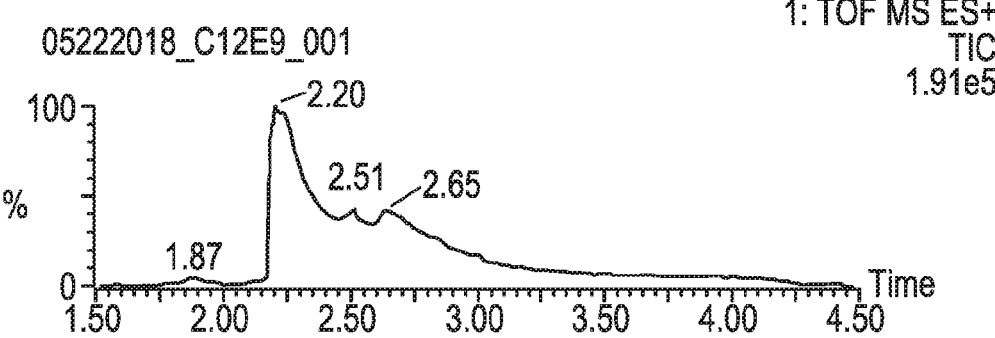
Figure 2F:
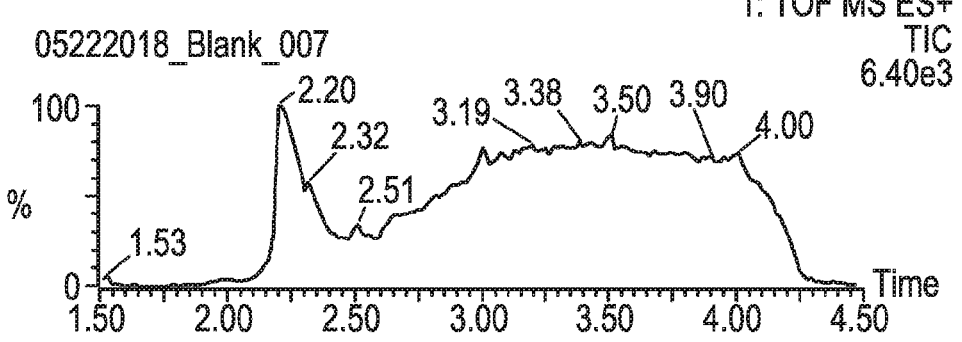

Manufacturing therapeutic biological drugs using cell culture processes carries an inherent risk of transmitting viral contaminants. Such contaminants can come from many sources, including starting materials, the use of reagents of animal origin during manufacture, and through contamination of the manufacturing system due to failures in the GMP process. As such, regulatory authorities recommend that biomanufacturing processes have dedicated virus inactivation and virus removal steps and request manufacturers validate the removal and inactivation of viruses from all biological products.

Provided herein is a method for inactivating envelope virus in a fluid known or suspected to contain at least one enveloped virus, comprising obtaining a fluid known or suspected to contain at least one enveloped virus; exposing the fluid to a detergent from Table 1; at a concentration and for a time sufficient to cause viral inactivation.

Provided herein is a provides a method for inactivating enveloped viruses during purification of a recombinant protein of interest comprising obtaining a fluid comprising the recombinant protein of interest which is known or suspected to contain at least one virus; subjecting the fluid to at least one detergent, wherein the detergent has a CAS registry number of CAS 3055-99-0, CAS 3055-98-9, CAS 9043-30-5, CAS 85618-20-8, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 69227-93-6, CAS 82494-09-5, CAS 253678-67-0, CAS 106402-05-5, or CAS 93911-12-7 at a concentration and for a time sufficient to cause inactivation of enveloped viruses in the fluid; and subjecting the viral inactivated fluid to at least one unit operation which includes at least a filtration step or a chromatography step.

Viruses are classified as enveloped and non-enveloped viruses. Enveloped viruses have a capsid enclosed by a lipoprotein membrane or "envelope". This envelope is made up of host cell proteins and phospholipids as well as viral glycoproteins which coat the virus as it buds from its host cell. This envelope allows the virus to identify, bind, enter, and infect target host cells. However, because of this membrane, enveloped viruses are susceptible to inactivation methods, while non-enveloped viruses are more difficult to inactivate without risk to the protein being manufactured, however, they can be removed by filtration methods.

Enveloped viruses include such virus families as herpesviridae virus, poxviridae virus, hepadnaviridae virus, flaviviridae virus, togaviridae virus, coronaviridae virus, orthomyxoviridae virus, deltavirus virus, paramyxoviridae virus, rhabdoviridae virus, bunyaviridae virus, filoviridae virus, retroviridae virus; and such viruses as human immunodeficiency virus, sindbis virus, herpes simplex virus, pseudorabies virus, sendai virus, vesicular stomatitis virus, West Nile virus, bovine viral diarrhea virus, a corona virus, equine arthritis virus, severe acute respiratory syndrome virus, Moloney murine leukemia virus, and vaccinia virus.

To ensure patient safety, viral inactivation is a necessary component of the purification process when manufacturing protein therapeutics. Various methods can be employed for virus inactivation and include heat inactivation/pasteurization, pH inactivation, UV and gamma ray irradiation, use of high intensity broad spectrum white light, addition of chemical inactivating agents, surfactants, and solvent/detergent treatments. Surfactants, such as detergents, solubilize membranes and therefore can be very effective in specifically inactivating enveloped viruses.

Detergents solubilize outer membranes of enveloped viruses by disrupting the protein layer with detergent micelles (Kragh-Hansen et al., Biophysical Journal 1998, 75 (6), 2932-2946). The outer layer of enveloped viruses, including xenotropic murine leukemia virus (xMuLV) and pseudorabies herpes viruses (PRV), is composed of a lipidic membrane that can be disrupted by certain detergents above their critical micelle concentration (CMC). Above the CMC, the detergent forms micelles, which disrupt the envelope layer by solubilizing the membrane lipids (Edwards and Almgren, Journal of Colloid and Interface Science 1991, 147 (1), 1-21).

Detergents can be classified by their charge into three groups: ionic, non-ionic, and zwitterionic. Both non-ionic and zwitterionic detergents are mild, and usually do not denature the therapeutic proteins being manufactured, while harsher, ionic detergents can degrade them. Historically, non-ionic detergents, such as the commonly used Triton X-100, have been used to inactivate virus because they do not affect the therapeutic proteins of interest. However, ecological concerns over use of certain detergents, such as Triton X-100, have driven the search to identify more "eco-friendly" detergents that can be used to inactivate enveloped virus in biomanufacturing processes.

As used herein "virus inactivation", "viral inactivation", "inactivate virus" or similar such phrases refer to a process where the enveloped virus is modified such that it can no longer infect cells, replicate, and/or propagate. Surfactants, such as detergents, are very effective in inactivating enveloped viruses in fluids known to contain or are suspected of containing one or more viruses. The fluid can be obtained from effluent streams, eluates, pools, hold or storage vessels. In one embodiment the fluid is obtained from a pool. In one embodiment the pool is obtained from a harvest unit operation that includes microfiltration. In one embodiment the fluid is obtained from an effluent stream.

Detergents can be added to the fluid at a concentration (w/v) of between 0.01% and 10%, or 0.01× to 10× of the detergent Critical Micelle Concentration (CMC) value. In certain embodiments the detergent concentration is at least 2.5×, at least 5×, at least 7.5× or at least 10× of the detergent CMC value.

The fluid can be exposed to the detergent at temperatures of at least 2° C. to 22° C. or higher. In certain embodiments the fluid is exposed to the detergent at a temperature of at least 2° C. or higher, at least 5° C. or higher, at least 7° C. or higher, at least 10° C. or higher, at least 15° C. or higher, at least 20° C. or higher, or at least 22° C. or higher. In certain embodiments the temperature is 2° C. to 22° C., 2° C. to 20° C., 2° C. to 15° C., 2° to 10° C., 2° C. to 7° C., or 2° C. to 5° C. In another embodiment the temperature is 5° C. to 22° C., 5° C., to 20° C., 5° C. to 15° C., 5° C. to 10° C., or 5° C. to 7° C. In another embodiment the temperature is 7° C. to 22° C., 7° C. to 20° C., 7° C. to 15° C., or 7° C. to 10° C. In another embodiment the temperature is 10° C. to 22° C., 10° C. to 20° C., or 10° C. to 15° C. In another embodiment the temperature is 10° C. to 22° C., 10° C. to 20° C., or 10° C. to 15° C. In another embodiment the temperature is 15° C. to 22° C., or 15° C. to 20° C. In one embodiment the temperature is 20° C. to 22° C. In certain embodiments the temperature is 2° C., 5° C., 7° C., 10° C., 15° C., 20° C., or 22° C. The fluid can be exposed to the detergent for as little as 30 seconds to 48 hours or longer. In certain embodiments the fluid is exposed to the detergent for at least 10, 15, 20, 25, 30, 35, 40, 45, 50, 55, 60, or 90 minutes. In certain embodiments the fluid is exposed to the detergent for 2, 3, 4, 5, 6, 9, 10, 12, 16, 20, 24, 30, 36, 42, or 48 hours. In certain embodiments, the fluid is exposed to the detergent for at least 30 seconds, at least 10 minutes, at least 30 minutes, at least 60 minutes, or at least 90 minutes. In certain embodiments the concentration is 2.5× of its CMC and the time is at least 10 minutes. In certain embodiments the concentration is 2.5× of its CMC and the time is at least 30 minutes. In certain embodiments the concentration is 5× of its CMC and the time is at least 10 minutes. In certain embodiments the concentration is 5× of its CMC and the time is at least 30 minutes.

Any degree of viral inactivation using the methods disclosed herein is desirable. However, it is preferred to achieve the degree of viral inactivation necessary to meet any safety guidelines or regulations for biopharmaceuticals as established by the relevant regulatory agency.

To determine the extent or effectiveness of an agent, such as the detergents described herein, to inactivate virus, one method is to monitor the impact on cytopathogenic effects (CPE). Cytopathic effects include structural changes in the host cell due to viral infection, such as host cell lysis, or cell death without lysis due to viral alterations that impact host cell division. If, after exposure to the agent, such effects in the host cell are not detectable, the virus is considered inactive. This may be measured using a $TCID_{50}$ assay which is used to determine the infectious titer of a virus which can cause cytopathic effects in a cell culture over a reasonable period, for example 5 to 20 days, while cells in culture remain viable. If active virus is present, the cytopathogenic effects on the cells can be observed using a microscope. The infected cells appear deformed and different from uninfected cells. The results are analyzed with a Spearman-Karber equation that provides a virus titer in each sample, which can then be used to calculate the total log reduction of virus. Inactivation is considered complete if it is not detected at the limit of the detection method being used, typically about 4 log 10.

As described herein, detergents with a wide range of structural variability, hydrophobicity and charge were evaluated for their effectiveness for inactivating enveloped viruses. Detergents with robust viral inactivation capability were identified. These include non-ionic detergents such as ANAPOE-C12E9; ANAPOE-C12E8; Alfonic TDA-6 Ethoxylate (TDA-6); Alfonic TDA-9 Ethoxylate (TDA-9); N-heptyl-β-D-thioglucopyranoside; n-Octyl-β-D-Thiomaltopyranoside; sucrose monolaurate; n-Decanoylsucrose; n-Octyl-β-D-Thioglucoside; CYMAL®-3; n-Tridecyl-β-D-maltoside; CYMAL®-6; hexaethylene glycol monooctyl ether; C-HEGA®-10; n-Undecyl-b-D-maltoside; n-Nonyl-b-D-thiomaltoside; HEGA®-9; ANAPOE-X-405; CYMAL®-5; C-HEGA®-11; Thesit; n-Nonyl-b-D-maltoside; MEGA-8; n-Nonyl-b-D-glucoside; HECAMEG®; HEGA®-10; n-Octyl-b-D-glucoside; HEGA®-8; MEGA-10; n-Dodecyl-b-D-maltoside; C8E5; MEGA-9; n-Hexyl-b-D-glucopyranoside; CYMAL®-7; CYMAL®-4; 2,6-Dimethyl-4-heptyl-b-D-malto-pyranoside; n-Decyl-b-D-maltoside; and C8E4. Zwitterion detergents including NDSB-195; FOS-MEA®-10; NDSB-201; CHAPS; NDSB-211; CHAPSO; NDSB-221; Fos-Choline®-10; NDSB-256; ZWITTERGENT® 3-08; Tripao and DDMAB. Synthetic lipid detergents including LysoFos™ Choline 12, Lyso-Fos™ Choline 14, Alfonic TDA-6 ethoxylate (Novel-TDA6, IsoC13E6), and Alfonic TDA-9 ethoxylate (Novel-TDA9, Iso-C13E9).

Among those detergents that were positive for viral inactivation against several enveloped viruses are some that are currently considered not dangerous as per European Union directive 67/548/EC pertaining to chemical safety; ANA-POE-C12E9 CAS Number: 3055-99-0; ANAPOE-C12E8 CAS Number: 3055-98-9; Alfonic TDA-6 Ethoxylate (TDA-6) CAS Number 9043-30-5; Alfonic TDA-9 Ethoxylate (TDA-9), CAS Number 9043-30-5; N-heptyl-β-D-thioglucopyranoside CAS Number: 85618-20-8; CYMAL®-3 CAS Number: 181135-58-0; CYMAL®-4 CAS Number: 181135-57-9; CYMAL®-5 CAS Number: 250692-65-0; CYMAL®-6 CAS Number: 228579-27-9; CYMAL®-7 CAS Number: 349477-49-2; Fos Choline®-10 CAS Number: 70504-28-8; n-Hexyl-b-D-glucopyranoside CAS Number: 59080-45-4; n-Nonyl-b-D-glucoside CAS Number: 69984-73-2; n-Octyl-β-D-Thiomaltopyranoside CAS Number: 148616-91-5; n-Nonyl-b-D-thiomaltoside CAS Number: 148565-55-3; n-Dodecyl-b-D-maltoside CAS Number: 69227-93-6; n-Decyl-b-D-maltoside CAS Number: 82494-09-5; n-Undecyl-b-D-maltoside CAS Number: 253678-67-0; n-Nonyl-b-D-thiomaltoside CAS Number: 106402-05-5;

n-Tridecyl-β-D-maltoside CAS Number: 93911-12-7; and n-Octyl-b-D-glucoside CAS Number: 29836-26-8.

Four groups of these "eco-friendly" detergents were chosen based on similar molecular structure and labeled as "CYMAL", "Fos-Choline", "Anapoe", and "Thiogluco-side", FIG. 1. Detergents from each of these groups were further analyzed for viral inactivation based on parameters including temperature, time, concentration, product modality, and virus type, as well as toxicity, and robust clearance of detergent.

Based on the large set of detergent viral inactivation data, trends affecting inactivation, including alkyl and ethoxylate chain length, were identified. Surprisingly, alkyl chain length affected viral inactivation activity. CYMAL®s having alkyl chains of one or two carbons had no effect on viral inactivation, while CYMAL®s having alkyl chains of 3-7 carbons did inactivate virus. A similar observation was made for Fos-Cholines®. Fos-Cholines® having an 8- or 9-carbon linker chain were found to have no effect on virus inactivation, whereas Fos-Choline® with a 10-carbon linker rendered the virus inactive. Anapoe detergents are composed of an alkyl chain and an ethoxylate chain where the number of alkyl carbons (C) and ethoxylate groups (E) are expressed within the name, e.g. Anapoe C12E9 has 12 alkyl carbons and 9 ethoxylate groups. While Anapoe C12E9 and Anapoe C12E8, Alfonic TDA-6 Ethoxylate (TDA-6) and Alfonic TDA-9 Ethoxylate (TDA-9), were found to robustly inactivate the virus, Anapoe C10E9, Anapoe C10E6, Anapoe C12E10 and C13E8 did not.

Anapoe C12E8, Anapoe C12E9, Alfonic TDA-6 Ethoxylate (TDA-6) and Alfonic TDA-9 Ethoxylate (TDA-9) and N-heptyl-β-D-thioglucopyranoside were particularly robust in viral inactivation in the presence of several important therapeutic modalities: monoclonal antibodies, bi-specific T-cell engagers (BiTEs®), and fusion proteins. These detergents showed complete viral inactivation at between 30 seconds and 30 minutes at temperatures as low as 5° C. and 15° C.

Detergent viral inactivation can take place at one or more steps of a biomanufacturing downstream process. Detergent viral inactivation can take place following harvest clarification and prior to an affinity chromatography step; following an affinity chromatography step and prior to a depth filtration and/or a polish chromatography step; in between polish chromatography steps; prior to a viral filtration step and/or a UF/DF step.

The terms "polynucleotide" or "nucleic acid molecule" are used interchangeably throughout and include both single-stranded and double-stranded nucleic acids and includes genomic DNA, RNA, mRNA, cDNA, or synthetic origin or some combination thereof which is not associated with sequences normally found in nature. The terms "isolated polynucleotide" or "isolated nucleic acid molecule" specifically refer to sequences of synthetic origin or those not normally found in nature. Isolated nucleic acid molecules comprising specified sequences may include, in addition to the sequences expressing the protein of interest, coding sequences for up to ten or even up to twenty other proteins or portions thereof or may include operably linked regulatory sequences that control expression of the coding region of the recited nucleic acid sequences, and/or may include vector sequences. The nucleotides comprising the nucleic acid molecules can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

As used herein, the term "isolated" means (i) free of at least some other proteins or polynucleotides with which it would normally be found, (ii) is essentially free of other proteins or polynucleotides from the same source, e.g., from the same species, (iii) separated from at least about 50 percent of polypeptides, polynucleotides, lipids, carbohydrates, or other materials with which it is associated in nature, (iv) operably associated (by covalent or noncovalent interaction) with a polypeptide or polynucleotide with which it is not associated in nature, or (v) does not occur in nature.

The terms "polypeptide" or "protein" are used interchangeably throughout and refer to a molecule comprising two or more amino acid residues joined to each other by peptide bonds. Polypeptides and proteins also include macromolecules having one or more deletions from, insertions to, and/or substitutions of the amino acid residues of the native sequence, that is, a polypeptide or protein produced by a naturally-occurring and non-recombinant cell; or is produced by a genetically-engineered or recombinant cell, and comprise molecules having one or more deletions from, insertions to, and/or substitutions of the amino acid residues of the amino acid sequence of the native protein. Polypeptides and proteins also include amino acid polymers in which one or more amino acids are chemical analogs of a corresponding naturally-occurring amino acid and polymers. Polypeptides and proteins are also inclusive of modifications including, but not limited to, glycosylation, lipid attachment, sulfation, gamma-carboxylation of glutamic acid residues, hydroxylation and ADP-ribosylation. The terms "isolated protein", "isolated recombinant protein", or "purified recombinant protein" may be used interchangeably and refer to a polypeptide or protein of interest, that is, purified away from proteins or polypeptides or other contaminants that would interfere with its therapeutic, diagnostic, prophylactic, research or other use. In particular, drug substances and drug products made from recombinant proteins of interest processed using the invention as described herein may be referred to as "recombinant protein drug products", "recombinant biologic therapeutics".

Polypeptides and proteins can be of scientific or commercial interest, including protein therapeutics. Proteins of interest include, among other things, secreted proteins, nonsecreted proteins, intracellular proteins or membrane-bound proteins. Proteins of interest can be produced by cell lines using methods described herein and may be referred to interchangeable as "recombinant proteins", "recombinant proteins of interest", or "recombinant protein therapeutics". The expressed protein(s) may be produced intracellularly or secreted into the culture medium from which it can be recovered and/or collected. Proteins of interest may include proteins that exert a therapeutic effect, for example, by binding a target, particularly a target among those listed below, including targets derived therefrom, targets related thereto, and modifications thereof.

Proteins of interest may include "antigen-binding proteins". Antigen-binding protein refers to proteins or polypeptides that comprise an antigen-binding region or antigenbinding portion that has a strong affinity for another molecule to which it binds (antigen). Antigen-binding proteins include, but are not limited to, antibodies, peptibodies, antibody fragments, antibody derivatives, antibody analogs, fusion proteins (including single-chain variable fragments (scFvs) and double-chain (divalent) scFvs, muteins, xMAbs, bispecific T cell engagers (BiTE®), and chimeric antigen receptors (CARs or CAR-Ts) and T cell receptors (TCRs).

An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen.

The term "antibody" includes reference to both glycosylated and non-glycosylated immunoglobulins of any isotype or subclass or to an antigen-binding region thereof that competes with the intact antibody for specific binding. Unless otherwise specified, antibodies include human, humanized, chimeric, multi-specific, monoclonal, polyclonal, heteroIgG, bispecific, and oligomers or antigen binding fragments thereof. Antibodies include the IgG1-, IgG2IgG3- or IgG4-type. Also included are proteins having an antigen binding fragment or region such as Fab, Fab', F(ab')2, Fv, diabodies, Fd, dAb, maxibodies, single chain antibody molecules, single domain $V_HH$, complementarity determining region (CDR) fragments, scFv, diabodies, triabodies, tetrabodies and polypeptides that contain at least a portion of an immunoglobulin that is sufficient to confer specific antigen binding to a target polypeptide.

Also included are human, humanized, and other antigenbinding proteins, such as human and humanized antibodies, that do not engender significantly deleterious immune responses when administered to a human.

Also included are modified proteins, such as are proteins modified chemically by a non-covalent bond, covalent bond, or both a covalent and non-covalent bond. Also included are proteins further comprising one or more post-translational modifications which may be made by cellular modification systems or modifications introduced ex vivo by enzymatic and/or chemical methods or introduced in other ways.

Proteins of interest may also include recombinant fusion proteins comprising, for example, a multimerization domain, such as a leucine zipper, a coiled coil, an Fc portion of an immunoglobulin, and the like. Also included are proteins comprising all or part of the amino acid sequences of differentiation antigens (referred to as CD proteins) or their ligands or proteins substantially similar to either of these.

In some embodiments, proteins of interest may include colony stimulating factors, such as granulocyte colonystimulating factor (G-CSF). Such G-CSF agents include, but are not limited to, Neupogen® (filgrastim) and Neulasta® (pegfilgrastim). Also included are erythropoiesis stimulating agents (ESA), such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, epoetin omega, epoetin iota, tissue plasminogen activator, GLP-1 receptor agonists, as well as the molecules or variants or analogs thereof and biosimilars of any of the foregoing.

In some embodiments, proteins of interest may include proteins that bind specifically to one or more CD proteins, HER receptor family proteins, cell adhesion molecules, growth factors, nerve growth factors, fibroblast growth factors, transforming growth factors (TGF), insulin-like growth factors, osteoinductive factors, insulin and insulinrelated proteins, coagulation and coagulation-related proteins, colony stimulating factors (CSFs), other blood and serum proteins blood group antigens; receptors, receptor-associated proteins, growth hormones, growth hormone receptors, T-cell receptors; neurotrophic factors, neurotrophins, relaxins, interferons, interleukins, viral antigens, lipoproteins, integrins, rheumatoid factors, immunotoxins, surface membrane proteins, transport proteins, homing receptors, addressins, regulatory proteins, and immunoadhesins.

In some embodiments proteins of interest bind to one of more of the following, alone or in any combination: CD proteins including but not limited to CD3, CD4, CD5, CD7, CD8, CD19, CD20, CD22, CD25, CD30, CD33, CD34, CD38, CD40, CD70, CD123, CD133, CD138, CD171, and CD174, HER receptor family proteins, including, for instance, HER2, HER3, HER4, and the EGF receptor, EGFRvIII, cell adhesion molecules, for example, LFA-1, Mol, p150,95, VLA-4, ICAM-1, VCAM, and alpha v/beta 3 integrin, growth factors, including but not limited to, for example, vascular endothelial growth factor ("VEGF"); VEGFR2, growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), Cripto, transforming growth factors (TGF), including, among others, TGF-$\alpha$ and TGF-$\beta$, including TGF-$\beta$1, TGF-$\beta$2, TGF-$\beta$3, TGF-$\beta$4, or TGF-$\beta$5, insulin-like growth factors-I and -II (IGF-I and IGF-II), des(1-3)-IGF-I (brain IGF-I), and osteoinductive factors, insulins and insulin-related proteins, including but not limited to insulin, insulin A-chain, insulin B-chain, proinsulin, and insulin-like growth factor binding proteins; (coagulation and coagulation-related proteins, such as, among others, factor VIII, tissue factor, von Willebrand factor, protein C, alpha-1-antitrypsin, plasminogen activators, such as urokinase and tissue plasminogen activator ("t-PA"), bombazine, thrombin, thrombopoietin, and thrombopoietin receptor, colony stimulating factors (CSFs), including the following, among others, M-CSF, GM-CSF, and G-CSF, other blood and serum proteins, including but not limited to albumin, IgE, and blood group antigens, receptors and receptor-associated proteins, including, for example, flk2/flt3 receptor, obesity (OB) receptor, growth hormone receptors, and T-cell receptors; (x) neurotrophic factors, including but not limited to, bone-derived neurotrophic factor (BDNF) and neurotrophin-3, -4, -5, or -6 (NT-3, NT-4, NT-5, or NT-6); (xi) relaxin A-chain, relaxin B-chain, and prorelaxin, interferons, including for example, interferon-alpha, -beta, and -gamma, interleukins (ILs), e.g., IL-1 to IL-10, IL-12, IL-15, IL-17, IL-23, IL-12/IL-23, IL-2Ra, IL1-R1, IL-6 receptor, IL-4 receptor and/or IL-13 to the receptor, IL-13RA2, or IL-17 receptor, IL-1RAP; (xiv) viral antigens, including but not limited to, an AIDS envelope viral antigen, lipoproteins, calcitonin, glucagon, atrial natriuretic factor, lung surfactant, tumor necrosis factor-alpha and -beta, enkephalinase, BCMA, IgKappa, ROR-1, ERBB2, mesothelin, RANTES (regulated on activation normally T-cell expressed and secreted), mouse gonadotropin-associated peptide, Dnase, FR-alpha, inhibin, and activin, integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, MIC (MIC-a, MIC-B), ULBP 1-6, EPCAM, addressins, regulatory proteins, immunoadhesins, antigen-binding proteins, somatropin, CTGF, CTLA4, eotaxin-1, MUC1, CEA, c-MET, Claudin-18, GPC-3, EPHA2, FPA, LMP1, MG7, NY-ESO-1, PSCA, ganglioside GD2, glanglioside GM2, BAFF, OPGL (RANKL), myostatin, Dickkopf-1 (DKK-1), Ang2, NGF, IGF-1 receptor, hepatocyte growth factor (HGF), TRAIL-R2, c-Kit, B7RP-1, PSMA, NKG2D-1, programmed cell death protein 1 and ligand, PD1 and PDL1, mannose receptor/hCG$\beta$, hepatitis-C virus, mesothelin dsFv [PE38 conjugate, *Legionella pneumophila* (lly), IFN gamma, interferon gamma induced protein 10 (IP10), IFNAR, TALL-1, thymic stromal lymphopoietin (TSLP), proprotein convertase subtilisin/Kexin Type 9 (PCSK9), stem cell factors, Flt-3, calcitonin gene-related peptide (CGRP), OX40L, $\alpha$4$\beta$7, platelet specific (platelet glycoprotein Iib/IIIb (PAC-1), transforming growth factor beta (TFG$\beta$), Zona pellucida sperm-binding protein 3 (ZP-3), TWEAK, platelet derived growth factor receptor alpha (PDGFR$\alpha$), sclerostin, and biologically active fragments or variants of any of the foregoing.

In another embodiment, proteins of interest include abciximab, adalimumab, adecatumumab, aflibercept, alemtuzumab, alirocumab, anakinra, atacicept, basiliximab, belimumab, bevacizumab, biosozumab, blinatumomab, brentuximab vedotin, brodalumab, cantuzumab mertansine, canakinumab, cetuximab, certolizumab pegol, conatumumab, daclizumab, denosumab, eculizumab, edrecolomab, efalizumab, epratuzumab, etanercept, evolocumab, galiximab, ganitumab, gemtuzumab, golimumab, ibritumomab tiuxetan, infliximab, ipilimumab, ixekizumab, lerdelimumab, lumiliximab, mapatumumab, motesanib diphosphate, muromonab-CD3, natalizumab, nesiritide, nimotuzumab, nivolumab, ocrelizumab, ofatumumab, omalizumab, oprelvekin, palivizumab, panitumumab, pembrolizumab, pertuzumab, pexelizumab, ranibizumab, rilotumumab, rituximab, romiplostim, romosozumab, sargamostim, tocilizumab, tositumomab, trastuzumab, ustekinumab, vedolizumab, visilizumab, volociximab, zanolimumab, zalutumumab, and biosimilars of any of the foregoing.

Proteins of interest according to the invention encompass all of the foregoing and further include antibodies comprising 1, 2, 3, 4, 5, or 6 of the complementarity determining regions (CDRs) of any of the aforementioned antibodies. Also included are variants that comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of a protein of interest. Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

Expression systems and constructs in the form of plasmids, expression vectors, transcription or expression cassettes that comprise at least one nucleic acid molecule as described above are also provided herein, as well host cells comprising such expression systems or constructs. As used herein, "vector" means any molecule or entity (e.g., nucleic acid, plasmid, bacteriophage, transposon, cosmid, chromosome, virus, virus capsid, virion, naked DNA, complexed DNA and the like) suitable for use to transfer and/or transport protein encoding information into a host cell and/or to a specific location and/or compartment within a host cell. Vectors can include viral and non-viral vectors, non-episomal mammalian vectors. Vectors are often referred to as expression vectors, for example, recombinant expression vectors and cloning vectors. The vector may be introduced into a host cell to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art.

"Cell" or "Cells" include any prokaryotic or eukaryotic cell. Cells can be either ex vivo, in vitro or in vivo, either separate or as part of a higher structure such as a tissue or organ. Cells include "host cells", also referred to as "cell lines", which are genetically engineered to express a polypeptide of commercial or scientific interest. Host cells are typically derived from a lineage arising from a primary culture that can be maintained in culture for an unlimited time. Genetically engineering the host cell involves transfecting, transforming or transducing the cells with a recombinant polynucleotide molecule, and/or otherwise altering (e.g., by homologous recombination and gene activation or fusion of a recombinant cell with a non-recombinant cell) to cause the host cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1990, and quarterly updates); Sambrook et al., Molecular Cloning: A Laboratory Manual (Cold Spring Laboratory Press, 1989); Kaufman, R. J., *Large Scale Mammalian Cell Culture,* 1990, pp. 15-69.

A host cell can be any prokaryotic cell (for example, *E. coli*) or eukaryotic cell (for example, yeast, insect, or animal cells (e.g., CHO cells)). Vector DNA can be introduced into prokaryotic or eukaryotic cells via conventional transformation or transfection techniques.

In one embodiment, the cell is a host cell. A host cell, when cultured under appropriate conditions, expresses the protein of interest that can be subsequently collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

By "culture" or "culturing" is meant the growth and propagation of cells outside of a multicellular organism or tissue. Suitable culture conditions for mammalian cells are known in the art. Cell culture media and tissue culture media are interchangeably used to refer to media suitable for growth of a host cell during in vitro cell culture. Typically, cell culture media contains a buffer, salts, energy source, amino acids, vitamins and trace essential elements. Any media capable of supporting growth of the appropriate host cell in culture can be used. Cell culture media, which may be further supplemented with other components to maximize cell growth, cell viability, and/or recombinant protein production in a particular cultured host cell, are commercially available and include RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series, among others, which can be obtained from the American Type Culture Collection or SAFC Biosciences, as well as other vendors. Cell culture media can be serum-free, protein-free, growth factor-free, and/or peptone-free media. Cell culture may also be enriched by the addition of nutrients and used at greater than its usual, recommended concentrations.

Various media formulations can be used during the life of the culture, for example, to facilitate the transition from one stage (e.g., the growth stage or phase) to another (e.g., the production stage or phase) and/or to optimize conditions during cell culture (e.g. concentrated media provided during perfusion culture). A growth medium formulation can be used to promote cell growth and minimize protein expression. A production medium formulation can be used to promote production of the protein of interest and maintenance of the cells, with a minimal of new cell growth). A feed media, typically a media containing more concentrated components such as nutrients and amino acids, which are consumed during the course of the production phase of the cell culture may be used to supplement and maintain an active culture, particularly a culture operated in fed batch, semi-perfusion, or perfusion mode. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount.

A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift.

Host cells may be cultured in suspension or in an adherent form, attached to a solid substrate. Cell cultures can be established in fluidized bed bioreactors, hollow fiber bioreactors, roller bottles, shake flasks, or stirred tank bioreactors, with or without microcarriers.

Cell cultures can be operated in a batch, fed batch, continuous, semi-continuous, or perfusion mode. Mammalian cells, such as CHO cells, may be cultured in bioreactors at a small scale of less than 100 ml to less than 1000 mls. Alternatively, large scale bioreactors that contain 1000 mls to over 20,000 liters of media can be used. Large scale cell cultures, such as for clinical and/or commercial scale biomanufacturing of protein therapeutics, may be maintained for weeks and even months, while the cells produce the desired protein(s).

Provided herein is a method for producing an isolated, purified, recombinant protein of interest comprising establishing a cell culture in a bioreactor with a host cell expressing a recombinant protein and culturing the cells to express the recombinant protein of interest; harvesting cell culture fluid containing the recombinant protein of interest; subjecting the harvested fluid containing the recombinant protein of interest to a detergent having a CAS registry number of CAS 3055-99-0, CAS 3055-98-9, CAS 9043-30-5, CAS 85618-20-8, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 69227-93-6, CAS 82494-09-5, CAS 253678-67-0, CAS 106402-05-5, or CAS 93911-12-7, at a detergent concentration and for a time sufficient to cause inactivation of enveloped virus; processing the viral inactivated fluid containing the recombinant protein of interest through at least two additional unit operations; and obtaining an isolated, purified, recombinant protein of interest.

Provided herein is a method for producing an isolated, purified, recombinant protein of interest comprising establishing a cell culture in a bioreactor with a host cell expressing a recombinant protein and culturing the cells to express the recombinant protein of interest; harvesting cell culture fluid containing the recombinant protein of interest; processing the harvested fluid containing the recombinant protein of interest through at least two unit operations, wherein during at least one unit operation there is a step where the fluid containing the recombinant protein of interest is combined with a detergent having a CAS registry number of CAS 3055-99-0, CAS 3055-98-9, CAS 9043-30-5, CAS 85618-20-8, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 69227-93-6, CAS 82494-09-5, CAS 253678-67-0, CAS 106402-05-5, or CAS 93911-12-7, at a detergent concentration and for a time sufficient to cause inactivation of enveloped virus; and obtaining an isolated, purified, recombinant protein of interest.

The cell culture fluid containing the expressed recombinant protein can then be harvested from the cell culture in the bioreactor. Methods for harvesting protein expressed from suspension cells are known in the art and include, but are not limited to, acid precipitation, accelerated sedimentation such as flocculation, separation using gravity, centrifugation, acoustic wave separation, filtration including membrane filtration using ultrafilters, microfilters, tangential flow filters, depth, and alluvial filtration filters. Recombinant proteins expressed by prokaryotes may be retrieved from inclusion bodies in the cytoplasm by redox folding processes known in the art.

The recombinant protein of interest in the clarified harvested cell culture fluid can then be purified, or partially purified, away from any impurities, such as remaining cell culture media, cell extracts, undesired components, host cell proteins, improperly expressed proteins, contaminants, microorganisms such as bacteria and viruses, aggregates, and the like, using one or more unit operations. The term "unit operation" refers to a functional step that is performed in a process for purifying a recombinant protein, such as from a liquid culture medium. For example, a unit of operation can involve filtering (e.g., removal of contaminant bacteria, yeast, virus, mycobacteria, impurities, and/or particulate matter from a fluid comprising a recombinant protein), capturing, epitope tag removal, purifying, collecting, holding, storing, polishing, harvesting, virus inactivating, including detergent viral inactivation, virus filtration, ionic concentration and/or pH adjustments of a fluid comprising the recombinant protein, and removal of unwanted salts. The invention described herein can be used at one or more steps in the down stream process from harvest to formulation of the drug substance.

For example, a unit operation can include steps such as, but not limited to, harvesting, capturing, purifying, polishing, viral inactivation, virus filtering, and/or adjusting the concentration and formulation containing the recombinant protein of interest. Unit operations can also include steps where fluid is pooled, held, and/or stored, such as capture pools, following harvest, chromatography or filtration, and fluid in holding or storing vessels, such as such as following harvest. A single unit operation may be designed to accomplish multiple objectives in the same operation, such as harvest and viral inactivation or capture and viral inactivation.

The capture unit operation includes capture chromatography that makes use of resins and/or membranes containing agents that will bind to the recombinant protein of interest, for example affinity chromatography, size exclusion chromatography, ion exchange chromatography, hydrophobic interaction chromatography (HIC), immobilized metal affinity chromatography (IMAC), and the like. Such materials are known in the art and are commercially available. Affinity chromatography may include, for example, a substrate-binding capture mechanism, an antibody- or antibody fragment-binding capture mechanism, an aptamer-binding capture mechanism, and a cofactor-binding capture mechanism, for example. Exemplary affinity chromatography includes a Protein A, Protein G, Protein A/G, or Protein L. The recombinant protein of interest can be tagged with a polyhistidine tag and subsequently purified from IMAC using imidazole or an epitope, such a FLAG® and subsequently purified by using a specific antibody directed to such epitope.

The one or more capture unit operations may include virus inactivation and virus filtration. In addition to the inventive viral inactivation methods provided herein, other methods for viral inactivation may also be used in addition such as heat inactivation/pasteurization, pH inactivation, UV and gamma ray irradiation, use of high intensity broad spectrum white light, and addition of chemical inactivating agents such as B-propiolactone.

The inactivation of viruses known or suspected to be contained in a fluid can be done at any time. During biological drug substance manufacturing, inactivation of virus in a fluid comprising a recombinant protein of interest can take place in one or more independent virus inactivation unit operations; as part of a harvest unit operation; prior to, as part of, or following one or more capture chromatography unit operations; prior to, as part of, or following one or more affinity chromatography unit operations; prior to, as part of, or following one or more polish chromatography unit operations; prior to, as part of, or following one or more ion exchange chromatography, hydrophobic interaction chromatography; mixed modal or multimodal chromatography, and/or hydroxyapatite chromatography unit operations; prior to, as part of, or following one or more virus filtration unit operations; and/or prior to or following one or more ultrafiltration/diafiltration unit operations. In one embodiment the viral inactivation takes place following harvest. In one embodiment the viral inactivation takes place following a harvest unit operation that includes microfiltration. In one embodiment the viral inactivation takes place prior to a capture chromatography unit operation. In one embodiment the viral inactivation takes place prior to a Protein A affinity chromatography step. Viral inactivation may be followed by filtration (such as depth filtration), or chromatography (such as Protein A chromatography), to remove inactivated viruses, inactivating agents such as surfactants and detergents, turbidity and/or precipitation.

Viral filtration can be performed using microfilters and/or nanofilters, which are available commercial sources such as Asahi Kasei (Plavona®) and EDM Millipore (VPro®).

The term "polishing" is used herein to refer to one or more chromatographic steps performed to remove remaining contaminants and impurities such as DNA, host cell proteins; product-specific impurities, variant products and aggregates and virus adsorption from a fluid including a recombinant protein that is close to a final desired purity. For example, polishing can be performed in bind and elute mode by passing a fluid including the recombinant protein through a chromatographic column(s) or membrane absorber(s) that selectively binds to either the target recombinant protein or the contaminants or impurities present in a fluid including a recombinant protein. In such an example, the eluate/filtrate of the chromatographic column(s) or membrane absorber(s) includes the recombinant protein.

The polish chromatography unit operation makes use chromatography resins and/or membranes containing agents that can be used in either a flow-through mode (where the protein of interest is contained in the eluent that flows through the chromatography medium and the contaminants and impurities are bound to the chromatography medium) or bind and elute mode (where the protein of interest is bound to the chromatography medium and eluted from the chromatography medium after the contaminants and impurities have flowed through or been washed off the chromatography medium). Examples of such chromatography methods include ion exchange chromatography (IEX), such as anion exchange chromatography (AEX) and cation exchange chromatography (CEX); hydrophobic interaction chromatography (HIC); mixed modal or multimodal chromatography (MM), hydroxyapatite chromatography (HA); reverse phase chromatography and gel filtration.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference. What is described in an embodiment of the invention can be combined with other embodiments of the invention.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

Virus Stocks

Viral stocks of xMuLV, PRV, and MMV were generated as previously described in Romanowski et al., Bioprocess Int 2008, 6 (2), 44-52. To identify cytopathic effects (CPE), an indicator cell line that is compatible with the virus was used. For xMuLV, the cell line PG4 (a feline astrocyte cell line) was used. CPE was determined seven days after inoculation. The cell line 324K was used to determine the CPE of MMV 10 days after inoculation, and for PRV, the Vero cell line was used in a 3-day assay.

Detergent Screen

An initial screen of 96 detergents was conducted using xMuLV, a murine retrovirus commonly used in viral clearance studies. The screen was carried out on a 96-deep well plate from Hampton Research (HR2-406), Aliso Viejo, CA The tested detergents had a range of amphoteric properties including non-ionic, zwitterionic, and ionic characteristics. All detergents evaluated in the screen were at 10× their Critical Micelle Concentration (CMC) value or 10% w/v, as indicated by the Hampton Kit. Duplicate runs of each detergent were evaluated after 30 minutes of a 5% virus spike at 15° C. A control with a 5% v/v water spike was also run simultaneously to show that the dilution was effective at stopping the detergent inactivation. Each of the replicate runs and the control run were diluted 1:300 with media, to reduce cytotoxicity and interference, and incubated with 25% confluent PG4 adherent cells. After an incubation period, wells were analyzed for any CPE in the inoculated PG4 cells.

A TCID50 assay was run with a 1:10 serial dilutions in 8 replicates from $10^0$-$40^{-7}$. A hold control solution of 10% xMuLV spiked into protein was held for the duration of the run without detergent, as well as a negative control of seed media. All samples were titrated with 25% confluent PG4 cells and incubated for 7 days at 37° C. Plates were read on the seventh day for CPE and evaluated with the Spearman-Karber equation for total virus titer and Logarithmic Reduction Values (LRVs), as previously described (Romanowski et al., supra).

Extended Viral Studies

Nineteen of the detergents that inactivated xMuLV are currently deemed not dangerous as per European Union directive 67/548/EC pertaining to chemical safety. These detergents were subjected to further testing at 5× the CMC value against two more viruses, another enveloped virus PRV and a non-enveloped virus MMV. Both viruses were tested at 5% v/v, otherwise the same conditions and assays as described for the initial detergent screen described above, were used.

Concentration Studies

Anapoe C12E8 (CAS Number 3055-98-9), Anapoe C12E9(CAS Number 3055-99-90), CYMAL®-5 (CAS Number 250692-65-0), Fos-Choline®-10 (CAS Number 70504-28-8), (supplied by Anatrace, Maumee, OH), and N-heptyl-β-D-thioglucopyranoside (CAS Number 85618-20-8), (Sigma-Aldrich, St. Louis, MO), were evaluated for the lowest concentration to still inactivate virus. Concentrations of 2.5×, 5×, and 7.5× the critical micelle concentration were evaluated against xMuLV at 15° C. with a 30-minute incubation period of detergent with virus as described above.

Temperature-Dependent Studies

Anapoe C12E8, Anapoe C12E9, CYMAL®-5, Fos-Choline-10, and N-heptyl-β-D-thioglucopyranoside were evaluated at temperatures from 5° C. to 22° C. against xMuLV and in matrices (host cell culture fluids) containing three different protein modalities, a monoclonal antibody (mAb #1), a bi-specific T cell engager (BiTE® #1), and a XmAb fusion protein (fusion protein #1). Time points of 30 seconds, 10 minutes, and 30 minutes were taken, and diluted 1:300, a dilution at which the buffer matrix does not cause toxicity and interference using the Spearman-Karber method, as previously described (Romanowski et al., supra). A Triton X100 control (Millipore Sigma, Temacula, CA) was run in duplicate at 18° C.

Kinetic Study of Detergents

Anapoe C12E8, Anapoe C12E9, CYMAL®-5, Fos-Choline-10, and N-heptyl-β-D-thioglucopyranoside were evaluated at three time points: 30 seconds, 10 minutes, and 30 minutes against xMuLV and in matrices (host cell culture fluids) containing three different protein modalities, a monoclonal antibody (mAb #1), a bi-specific T cell engager (BiTE® #1), and a XmAb fusion protein (fusion protein #1). Time points of 30 seconds, 10 minutes, and 30 minutes were taken, and diluted 1:300, a dilution at which the buffer matrix does not cause toxicity and interference using the Spearman-Karber method.

Detergent Clearance

Clearance of the detergent Anapoe C12E9 was evaluated during Protein A chromatography against a sample containing a monoclonal antibody. Protein samples (host cell culture fluids containing the monoclonal antibody) were spiked with 0.03% detergent and run through a Protein A column Elution peak, and buffer spiked with detergent were evaluated for clearance on a Waters BioResolve™ Polyphenol (Milford, MA) 450 Å, 2.1×50 mm column. The flow rate was 0.5 mL/min at 65° C. A gradient of 5 minutes with a stationary phase A of water with 0.1% TFA/0.1% formic acid, and 90% n-propanol as mobile phase B was used to run samples.

Extended Scope Study

The scope of the study was extended to evaluate two more alkyl ethoxylate derivatives. Alkyl ethoxylate detergents IsoC13E6 (CMC: 29.91 mg/L) and Iso-C13E9 (CMC: 57.97 mg/L), also available as Alfonic TDA-6 ethoxylate, Novel-TDA6 and Alfonic TDA-9 ethoxylate, Novel-TDA9, (Avantor, Radnor, PA; Sasol, Johannesburg, South Africa), CAS 9043-30-5), were tested at three concentrations: 2.5×, 5×, and 7.5× their CMC value. Samples were incubated with host cell culture fluid containing either mAb #1 or bispecific T cell engager (BiTE®#1) at 5° C. with a 5% XMuLV spike. Samples were diluted 1:300 to reduce cytotoxicity and interference at three-time points: 30 seconds, 10 minutes, and 30 minutes.

A TCID50 assay was run with 1:10 serial dilutions in 8 replicates from $10^0 10^{-7}$. A hold control solution of 5% XMuLV spiked into protein was held for the duration of the run without detergent, as well as a negative control of seed media. All samples were titrated with 25% confluent PG4 cells and incubated for 7 days at 37° C. Plates were read on the seventh day for CPE and evaluated with the Spearman-Karber equation for total virus titer and Logarithmic Reduction Values (LRVs), as previously described (Romanowski et al., supra).

Results and Discussion

Detergent Screen

Utilizing a commercially available selection of 96 detergents with varying ionic, hydrophobic, and structural characteristics, an initial screen was carried out against an enveloped model virus, xMuLV. Fifty-one of these detergents, no CPE was identified in both duplicates and the detergent control as shown in Table 1. This group included non-ionic, zwitterionic, and synthetic lipid detergents, whereas none of the ionic detergents tested showed viral inactivation.

TABLE 1

Detergents that showed viral inactivation towards xMuLV from initial 96 sample detergent screen.

| Detergent | CMC (mM) | Concentration (mM or % w/v) | cLogP | Type |
|---|---|---|---|---|
| ANAPOE-C12E9 | 0.05 | 0.5 | 3.6678 | N |
| ANAPOE-C12E8 | 0.11 | 1.1 | 3.8434 | N |
| N-heptyl-β-D-thioglucopyranoside | 29 | 290 | 2.01455 | N |
| n-Octyl-β-D-Thiomaltopyranoside | 8.8 | 85 | 0.3578 | N |
| NDSB-195 | n/a | 0.5 | −8.136 | Z |
| FOS-MEA ®-10 | 5.25 | 52.5 | −0.169 | Z |
| Sucrose monolaurate | 0.3 | 3 | 2.44925 | N |
| n-Decanoylsucrose | 2.5 | 25 | 1.39125 | N |
| n-Octyl-β-D-Thioglucoside | 9 | 90 | 2.54355 | N |
| CYMAL ®-3 | 34.5 | 345 | −0.2037 | N |
| NDSB-201 | n/a | 0.5 | −8.8248 | Z |
| CHAPS | 8 | 80 | −5.265 | Z |
| n-Tridecyl-β-D-maltoside | 0.033 | 0.33 | 2.4363 | N |
| CYMAL ®-6 | 0.56 | 5.6 | 1.3833 | N |
| Hexaethylene glycol monooctyl ether | 10 | 100 | 2.0786 | N |
| C-HEGA ®-10 | 35 | 350 | 2.1348 | N |
| NDSB-211 | n/a | 0.5 | −7.7726 | Z |
| CHAPSO | 8 | 80 | −5.7552 | Z |
| n-Undecyl-b-D-maltoside | 0.59 | 5.9 | 1.3783 | N |

TABLE 1-continued

Detergents that showed viral inactivation towards xMuLV from initial 96 sample detergent screen.

| Detergent | CMC (mM) | Concentration (mM or % w/v) | cLogP | Type |
|---|---|---|---|---|
| n-Nonyl-b-D-thiomaltoside | 3.2 | 32 | 0.886797 | N |
| HEGA ®-9 | 39 | 390 | 2.1298 | N |
| NDSB-211 | n/a | 0.5 | −7.072 | Z |
| FOS-Choline ®-10 | 11 | 110 | −5.557 | Z |
| ANAPOE-X-405 | 0.81 | 10% | −2.2674 | N |
| CYMAL ®-5 | 5 | 50 | 0.8543 | N |
| C-HEGA ®-11 | 11.5 | 115 | 2.6638 | N |
| NDSB-256 | n/a | 0.5 | −6.257 | Z |
| Thesit | 0.09 | 0.9 | | N |
| n-Nonyl-b-D-maltoside | 6 | 60 | 0.3203 | N |
| MEGA-8 | 79 | 790 | 1.803 | N |
| n-Nonyl-b-D-glucoside | 6.5 | 65 | 2.50605 | N |
| HECAMEG ® | 19.5 | 195 | 1.57255 | N |
| C-HEGA ®-9 | 108 | 1080 | 1.6058 | N |
| HEGA ®-10 | 7 | 70 | 2.6588 | N |
| n-Octyl-b-D-glucoside | 20 | 200 | 1.97705 | N |
| HEGA ®-8 | 109 | 1090 | 1.6008 | N |
| MEGA-10 | 7 | 70 | 2.861 | N |
| n-Dodecyl-b-D-maltoside | 0.17 | 1.7 | 1.9073 | N |
| C8E5 | 7.1 | 71 | 2.2542 | N |
| MEGA-9 | 25 | 250 | 2.332 | N |
| n-Hexyl-b-D-glucopyranoside | 250 | 2500 | 0.919 | N |
| ZWITTERGENT ® 3-08 | 330 | 10% | −4.962 | Z |
| CYMAL ®-7 | 0.19 | 1.9 | 1.9123 | N |
| CYMAL ®-4 | 7.6 | 76 | 0.3253 | N |
| 2,6-Dimethyl-4-heptyl-b-D-malto-pyranoside | 27.5 | 275 | −0.1597 | N |
| Tripao | 4.5 | 45 | 5.9888 | Z |
| LysoFos ™ Choline 12 | 0.7 | 7 | −6.4146 | SL |
| n-Decyl-b-D-maltoside | 1.8 | 18 | 0.8493 | N |
| C8E4 | 8 | 80 | 1.9008 | N |
| DDMAB | 4.3 | 43 | −1.831 | Z |
| LysoFos ™ Choline 14 | 0.036 | 0.36 | −5.3566 | SL |

SL = Synthetic Lipid; Z = Zwitterionic; N = Non-ionic.

Of the 51 detergents found positive for viral inactivation, some were similar in structure, only varying by an alkyl chain linker length. By evaluating the results based on detergent structure, trends within structural classes were observed. Nineteen of the identified detergents are currently deemed not dangerous as per European Union directive 67/548/EC pertaining to chemical safety (Table 2). These "eco-friendly" detergents were grouped into four classes based on molecular structure and labeled as CYMAL, Fos-Choline, Anapoe and Thioglucoside, FIG. 1.

TABLE 2

Detergents that were positive for viral inactivation and are deemed not dangerous as per European Union directive 67/548/EC pertaining to chemical safety

| | |
|---|---|
| Anapoe C12E9 | n-Nonyl-b-D-glucoside |
| Polyoxyethylene(9)dodecyl ether | CAS Number: 69984-73-2 |
| Polydocanol | |
| α-dodecyl-w-hydroxy-poly(ocy-1,2-ethanediyl) | |
| CAS Number: 3055-99-0 | |
| Anapoe C12E8 | n-Octyl-β-D-Thiomaltopyranoside, |
| Polyoxyethylene(8)dodecyl ether | CAS Number: 148616-91-5 |
| 3,6,9,12,15,18,21,24-oxtaoxahexatriacontan-1-ol | |
| CAS Number: 3055-98-9 | |
| N-heptyl-β-D-thioglucopyranoside | n-Nonyl-b-D-thiomaltoside |
| Heptyl thioglucoside | CAS Number: 148565-55-3 |
| Heptyl-β-D-1-thioglucopyranoside | |
| CAS Number: 85618-20-8 | |
| CYMAL ®-3 | n-Dodecyl-b-D-maltoside |
| 3-Cyclohexyl-1-Propyl-β-D-Maltoside | CAS Number: 69227-93-6 |
| 3-Cyclohexylpropyl-4-O-(a-D-glucopyranosyl)-b-D-glucopyranoside | |
| 3-cyclohexylpropyl 4-O-alpha-D-glucopyranosyl-beta-D-glucopyranoside | |
| (2R,3R,4S,5S,6R)-2-[(2R,3S,4R,5R,6R)-6-(3-cyclohexylpropoxy)-4,5-dihydroxy-2-(hydroxymethyl)oxan-3-yl]oxy-6- | |

TABLE 2-continued

Detergents that were positive for viral inactivation and are deemed not dangerous as per European
Union directive 67/548/EC pertaining to chemical safety

| | |
|---|---|
| (hydroxymethyl)oxane-3,4,5-triol CAS Number: 181135-58-0 | |
| CYMAL ®-4 4-Cyclohexyl-1-Butyl-β-D-Maltoside 4-Cyclohexylbutyl-4-O-(a-D-glucopyranosyl)-b-D-glucopyranoside 4-cyclohexylbutyl 4-O-alpha-D-glucopyranosyl-beta-D-glucophranoside CAS Number: 181135-57-9 | n-Decyl-b-D-maltoside CAS Number:82494-09-5 |
| CYMAL ®-5 5-cyclohexylpentyl-β-D-maltoside CAS Number: 250692-65-0 | n-Undecyl-b-D-maltoside CAS Number: 253678-67-0 |
| CYMAL ®-6 6-cyclohexyl-1-hexyl-β-D-maltoside CAS Number: 228579-27-9 | n-Nonyl-b-D-maltoside CAS Number: 106402-05-5 |
| CYMAL ®-7 7-cyclohexyl-l-heptyl-β-D-maltoside CAS Number: 349477-49-2 | n-Tridecyl-β-D-maltoside CAS Number: 93911-12-7 |
| Fos-Choline ®-10 n-decylphosphocholine CAS Number: 70504-28-8 n-Hexyl-b-D-glucopyranoside CAS Number: 59080-45-4 | n-Octyl-b-D-glucoside CAS Number: 29836-26-8 |

CYMAL® detergents contain a maltoside sugar linked by alkyl chains of varying length to cyclohexane. CYMAL®s 1-7 were among the 96 detergents in the initial screen. Surprisingly, CYMAL®s having alkyl chains of one or two carbons had no effect on inactivating the xMuLV virus, however CYMAL®s having alkyl chains of 3-7 carbons did inactivate the virus. A similar surprising result related to alkyl chain lengths affecting Fos-Cholines and Anapoe derivatives was seem as well. Fos-Cholines having an 8- or 9-carbon linker chain were found to have no effect on virus inactivation, whereas Fos-Choline with a 10-carbon linker rendered the virus inactive. Anapoe detergents are composed of an alkyl chain and an ethoxylate chain where the number of alkyl carbons (C) and ethoxylate groups (E) are expressed within the name, e.g. Anapoe C12E9 has 12 alkyl carbons and 9 ethoxylate groups. While Anapoe C12E9 and Anapoe C12E8 were found to robustly inactivate the virus, Anapoe C10E9, Anapoe C10E6, Anapoe C12E10 and C13E8 did not, Table 3. Alkyl chain length attributes to the overall hydrophobicity of the molecule and may ultimately affect viral envelope partitioning. A specific range of lipophilicity may be necessary to induce rupture of the lipidic envelope layer.

TABLE 3

Alkyl chain length affecting viral inactivation of xMuLV

| Viral Inactivation | No Viral Inactivation |
|---|---|
| CYMAL ®-3 | CYMAL ®-1 |
| CYMAL ®-4 | CYMAL ®-2 |
| CYMAL ®-5 | Fos-Choline 8 |
| CYMAL ®-6 | Fos-Choline 9 |
| CYMAL ®-7 | Fos-Choline 8 Fluorinated |
| Fos-Choline ®-10 | Anapoe C10E9 |
| Anapoe C12E8 | Anapoe C10E6 |
| Anapoe C12E9 | Anapoe C13E8 |
| | Anapoe C12E10 |

Extended Virus Study Scope of Viral Inactivation

The 19 "eco-friendly" detergents were further tested with a different enveloped virus, PRV, and a non-enveloped virus, mouse minute virus (MMV). All 19 detergents inactivated PRV as they did xMuLV, but had no effect on MMV, indicating the detergents affect enveloped viruses, but not unenveloped viruses. Triton X-100 also only affects enveloped viruses, indicating these detergents likely disrupt the lipidic envelope in a similar manner.

Concentration Studies

To determine the lowest concentration necessary for inactivation of xMuLV; CYMAL®-5, Anapoe C12E8, Anapoe C12E9, FosCholine®-10, and N-heptyl-β-D-thioglucopyranoside, were tested in duplicate at 2.5×, 5×, and 7.5× their CMC value, against xMuLV, PRV and MMV. For all viruses tested, 2.5×CMC showed cytopathic effects (CPE); therefore, subsequent studies were evaluated at 5× the detergent CMC value.

Temperature-Dependent Studies

Anapoe C12E8, Anapoe C12E9, N-heptyl-β-D-thioglucopyranoside, CYMAL®-5, and Fos-Choline®-10 were analyzed in the presence of three protein therapeutic modalities, a monoclonal antibody (mAb), a bi-specific T cell enhancer (BiTE®) and a fusion protein (XmAb), at various temperatures (Table 2). Both Anapoe detergents and N-heptyl-β-D-thioglucopyranoside showed complete inactivation at 30 minutes at both 5° C. and 15° C., which represent the "worst-case scenario" temperatures for a manufacturing environment. These three detergents have comparable LRV values to Triton X-100 for both BiTE® and mAb modalities, and even better clearance for the fusion protein.

The detergents FosCholine-10 and CYMAL®-5 did not yield significant inactivation towards xMuLV at any temperature tested. Since virus inactivation with these detergents was observed during the initial detergent screen and other experiment, when no product was present, there may be negative interactions with the sample matrix. At a process temperature of 15° C., Fos-Choline®-10 and CYMAL®-5 had an average LRV of 3.8, and 0.39, respectively. To parse out the effect temperature had on the detergents, CYMAL®-5 was tested at a higher temperature (22° C.), which did lead to ~1 log increase in LRV. Even with this temperature increase, the LRV was still low.

TABLE 4

Log Reduction values for five detergents tested at two temperatures (5° C. and 15° C.) against three different modalities. LRVs were compared to Triton X-100, which has robust xMuLV clearance.

| Product | Temp (° C.) | LRV | | |
|---|---|---|---|---|
| | | BiTE ® | mAb | fusion protein |
| FosCholine ®-10 | 5 | 2.09 ± 0.31 | 2.54 ± 0.34 | 1.76 ± 0.41 |
| | 15 | 3.92 ± 0.67 | 3.97 ± 0.90 | 3.51 ± 0.43 |
| CYMAL ®-5 | 15 | −0.06 ± 0.69 | 0.62 ± 0.50 | 0.62 ± 0.48 |
| | 22 | 1.19 ± 0.29 | 1.94 ± 0.52 | 1.01 ± 0.45 |
| Anapoe C12E8 | 5 | ≥4.03 ± 0.18 | ≥4.41 ± 0.37 | ≥4.23 ± 0.33 |
| | 15 | ≥4.32 ± 0.35 | ≥3.28 ± 0.34 | ≥4.99 ± 0.42 |
| Anapoe C12E9 | 5 | ≥3.84 ± 0.33 | ≥3.91 ± 0.30 | ≥4.19 ± 0.25 |
| | 15 | ≥3.91 ± 0.43 | ≥4.23 ± 0.38 | ≥4.32 ± 0.36 |
| N-heptyl-B-D- | 5 | ≥4.23 ± 0.33 | ≥4.09 ± 0.25 | ≥4.07 ± 0.30 |
| Thioglucopyranoside | 15 | ≥4.03 ± 0.18 | ≥4.22 ± 0.41 | ≥4.16 ± 0.42 |
| Triton X-100 Run 1 | 2-18* | 5.85 ± 0.92** | ≥4.49 ± 0.37** | 5.03 ± 0.58** |
| Triton X-100 Run 2 | 2-18* | ≥5.62 ± 0.40** | ≥4.82 ± 0.44** | 5.04 ± 0.57** |

*The BiTE ® protein was tested at 18° C., mAb tested at 2° C., and fusion protein tested at 7° C.
**LRV values were based on an 800-sample large volume plate, which leads to 1 LRV increase from the 80 wells that were tested for the alternative detergents.

Kinetic Study of Detergents

To evaluate the rate at which virus inactivation is occurring, three time points were tested: 30 seconds, 10 minutes, and 30 minutes. Within 30 seconds, complete inactivation of xMuLV was observed for Anapoe C12E8 and N-heptyl-β-D-thioglucopyranoside against all three therapeutic modalities tested. Anapoe C12E9 displayed complete inactivation at 30 seconds against mAb #1, and complete inactivation within 10 minutes against fusion protein #1 and BiTE® #1, see Table 5. Anapoe C12E9 showed complete clearance within 10 minutes for all three therapeutic modalities tested. Anapoe C12E9 has a CMC value half that of Anapoe C12E8, meaning it requires significantly less detergent to achieve the same LRV. For scale-up to commercial manufacturing quantities, this attribute would be of significant benefit.

Both Fos-Choline-10 and CYMAL®-5 did not lead to robust clearance within 30 minutes.

Clearance of Anapoe C12E8

To ensure the detergent can be completely cleared after the viral inactivation process, host cell culture fluid containing a mAb was spiked with 0.03% Anapoe C12E8 detergent was affinity purified using Protein A chromatography. Liquid Chromatography-Mass Spectrometry (LC-MS) was used to analyze the amount of detergent left after the chromatography run. The results indicate the detergent is cleared during the Protein A chromatography step, FIG. 2.

Extended Scope of Alkyl Ethoxylate Detergents

To further understand the specificity of detergent necessary for robust viral clearance, two more alkyl ethoxylates, that incorporated a branched, isopropyl group, were evaluated. Both detergents also had robust clearance of xMuLV at concentrations at or above 5×CMC value. High LRVs were observed with two therapeutic modalities, mAb #1 and BiTE® #1, Table 6. These results indicate the robust viral inactivation capability of a wide scope of Anapoe derivatives.

TABLE 5

Log reduction values (LRVs) for detergents tested against three products taken at three time points; 30 seconds, 10 minutes and 30 minutes.

| Detergent at 15° C. | Product | LRV | | |
|---|---|---|---|---|
| | | 30 s | 10 min | 30 min |
| FosCholine ®-10 | BiTE ® #1 | 0.69 ± 0.44 | 1.57 ± 0.47 | 3.92 ± 0.67 |
| | mAb #1 | 0.69 ± 0.31 | 1.61 ± 0.56 | 3.97 ± 0.90 |
| | fusion protein #1 | 0.82 ± 0.57 | 1.82 ± 0.51 | 3.51 ± 0.43 |
| CYMAL ®-5 | BiTE ® #1 | 0.19 ± 0.69 | 0.06 ± 0.58 | −0.06 ± 0.69 |
| | mAb #1 | 0.25 ± 0.58 | 0.12 ± 0.58 | 0.62 ± 0.50 |
| | fusion protein #1 | −0.06 ± 0.69 | 0.31 ± 0.52 | 0.62 ± 0.48 |
| Anapoe C12E8 | BiTE ® #1 | ≥3.32 ± 0.35 | ≥3.32 ± 0.35 | ≥3.32 ± 0.35 |
| | mAb #1 | ≥3.28 ± 0.34 | ≥3.28 ± 0.34 | ≥3.28 ± 0.34 |
| | fusion protein #1 | ≥3.99 ± 0.42 | ≥3.99 ± 0.42 | ≥3.99 ± 0.42 |
| Anapoe C12E9 | BiTE ® #1 | 2.61 ± 0.68 | ≥2.91 ± 0.43 | ≥2.91 ± 0.43 |
| | mAb #1 | ≥3.23 ± 0.00 | ≥3.23 ± 0.00 | ≥3.23 ± 0.00 |
| | fusion protein #1 | 2.56 ± 0.60 | ≥3.32 ± 0.36 | ≥3.32 ± 0.36 |
| N-heptyl-β-D- | BiTE ® #1 | ≥3.03 ± 0.18 | ≥3.03 ± 0.18 | ≥3.03 ± 0.18 |
| Thioglucopyranoside | mAb #1 | ≥3.22 ± 0.41 | ≥3.22 ± 0.41 | ≥3.22 ± 0.41 |
| | fusion protein #1 | ≥3.16 ± 0.42 | ≥3.16 ± 0.42 | ≥3.16 ± 0.42 |

TABLE 6

Samples were incubated at 5° C. for 30 min at three concentrations with product. Complete inactivation of XMuLV was observed with 5× the CMC value of both Iso-C13E6 (Alfonic TDA-6 ethoxylate Novel-TDA6) and Iso-C13E9 (Alfonic TDA-9 ethoxylate, Novel-TDA9).

| Detergent | CMC Value (mg/L) | Concentration (xCMC Value) | Concentration (mg/L) | LRV | Product |
|---|---|---|---|---|---|
| Iso-C13E6, | 29.91 | 2.5 | 74.8 | 4.9 ± 0.33 | mAb #1 |
| Alfonic TDA-6 | | 5 | 149.6 | ≥4.37 ± 0.31 | |
| ethoxylate, | | 7.5 | 224.4 | ≥4.37 ± 0.40 | |
| Novel-TDA6 | | | | | |
| Iso-C13E9, | 57.97 | 2.5 | 145 | 3.64 ± 0.54 | BiTE ® #1 |
| Alfonic TDA-9 | | 5 | 290 | ≥4.12 ± 0.35 | |
| ethoxylate, | | 7.5 | 435 | ≥4.37 ± 0.37 | |
| Novel-TDA9 | | | | | |

Example 2 Turbidity

Three detergents were further tested to determine if they negatively impacted the stability of four different protein modalities, as measured by turbidity, solubility and high molecular weight species (HMW). In addition, product quality as measured by size exclusion chromatography (SEC-HPLC) for HMW and reduced capillary electrophoresis-sodium dodecyl sulfate (rCE-SDS) for low molecular weight species (LMW).

Anapoe C12E8 (APO128), Anapoe C12E9 (APO129), and Triton X-100 were tested using a monoclonal antibody (mAb #2), two fusion proteins (fusion #2 and fusion #3), a bispecific (bispecific #1), and two bispecific T cell engagers (BiTE® #1 and BiTE® #2).

Determination of turbidity was used to measure the stability of detergent spiked samples. Increased turbidity of the sample would reflect a precipitation of the protein molecule. 100 mL of harvested cell culture fluid (HCCF) collected from cultures of each molecule were subjected to four conditions: HCCF containing no detergent (control), APO128, APO129 and Triton X-100. The detergents were spiked at five times the detergent's critical micelle concentration (CMC) values, Triton-X: Triton-X: 1.1 mM, APO128: 0.55 mM, APO 129: 0.25 mM, TDA-9:0.48 mM.

Two sample sets were generated for each molecule; one set was kept at room temperature for 5 days. The second set was kept at 2-8° C. for 7 days. The turbidity of each sample was measured using a turbidimeter (Hach Turbidimeter 2100P 46500-00, Loveland, CO) on days 0, 1, 2, 5, and 7.

Figures 3A, 3B, 3C, 3D:
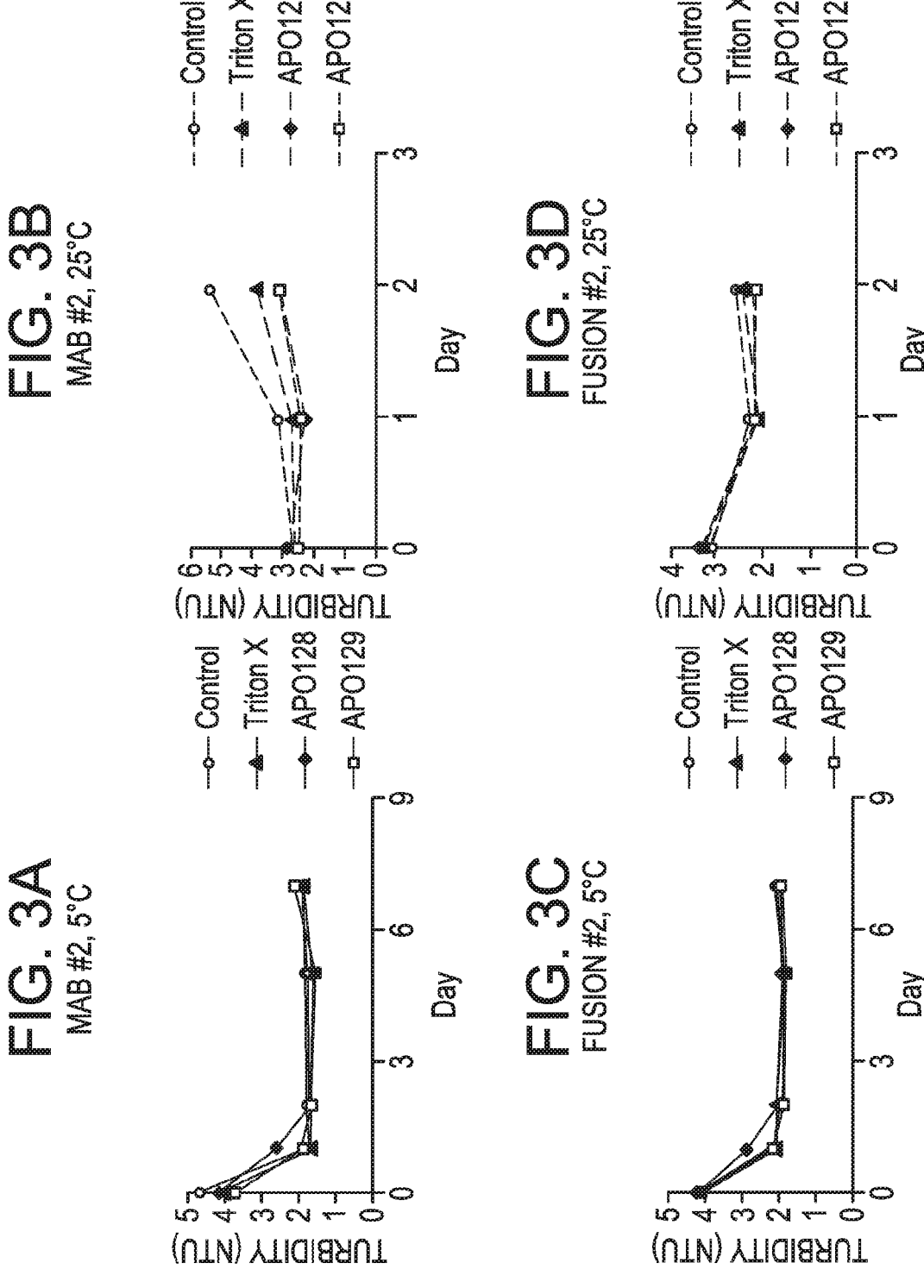
FIG. 3: Turbidity data for a mixture of detergents and HCCF at room temperature (25° C.) and at 5° C. Triton X, triangle; Anapoe C12E8 (APO128), diamond; Anapoe C12E8 (APO129), square; no detergent control, circle.
Figures 3I, 3J, 3K, 3L:
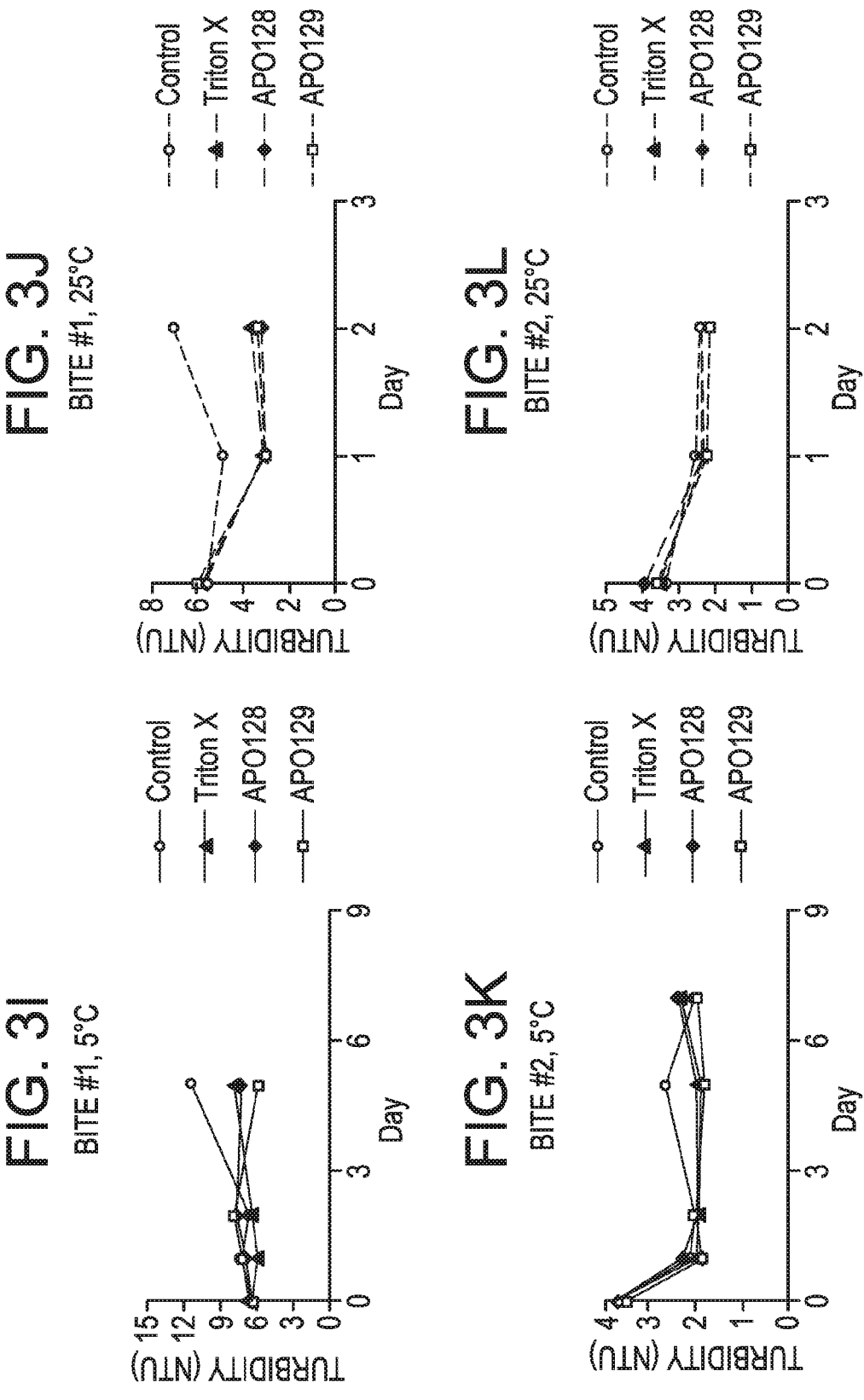

FIG. 3 shows turbidity data at each time point for a mixture of detergents and HCCF at room temperature and at 2-8° C. Data points for room temperature at day 5 show the greatest variability, which may be due to bacterial contamination of the samples. The data points from samples spiked with APO128 and APO129 trended very closely with data points from samples spiked with Triton X-100 or were less turbid than the control. This indicates that none of the detergents tested caused precipitation of the different protein modalities.

Experiment 4 Product Quality

Percent high molecular weight (% HMW) and percent low molecular weight (% LMW) were used to measure the stability of detergent spiked samples. % HMW measured aggregation of the protein in a sample, while % LMW measured clipping of the protein. These product quality attributes were measured before and after affinity column purification to determine if the presence of detergent affects the affinity purification process or product quality of affinity purified material.

Harvested cell culture fluid and post-affinity chromatography samples from a monoclonal antibody (mAb #2), two fusion proteins (fusion #2 and fusion #3), a bispecific (bispecific #1), and two bispecific T cell engagers (BiTE® #1 and BiTE® #2) were tested.

100 mL samples of the HCCF pre-affinity chromatography load material and post-affinity chromatography pool material were spiked with five times the critical micelle concentration (CMC) with Anapoe C12E8 (APO128) (0.11 mM), Anapoe C12E9 (APO129) (0.05 mM), Alfonic TDA-9 Ethoxylate (TDA-9) (0.1 mM) and Triton X-100 (0.22 mM). A no detergent sample was used as a control. Samples were stirred in room temperature with the detergent for ~1 hour. They were then either kept in 2-8° C. for 7 days before submitting for product quality analysis, or purified via affinity column and then submitted for product quality analysis.

Post-affinity column samples were generated by subjecting the harvested cell culture fluid to Protein A affinity chromatography using a GE CaptoChelating resin (Pittsburgh, PA) for BiTE #2 and a GE MabSelect Sure resin (Pittsburgh, PA), for all other protein modalities.

An additional 100 mL sample of HCCF pre-affinity chromatography load material from each protein modality was spiked with detergent and kept at 2-8° C. for 7 days.

Product quality was assessed using SEC-HPLC to determine % HMW and rCE-SDS to determine % LMW.

Due to the timing of material availability, two sets of experiments were performed. The first experiment comprised four conditions: a no detergent control, Triton X-100, APO128, and APO129. The second experiment comprised two conditions: a no detergent control and TDA-9.

Figures 4E, 4F, 4G, 4H:
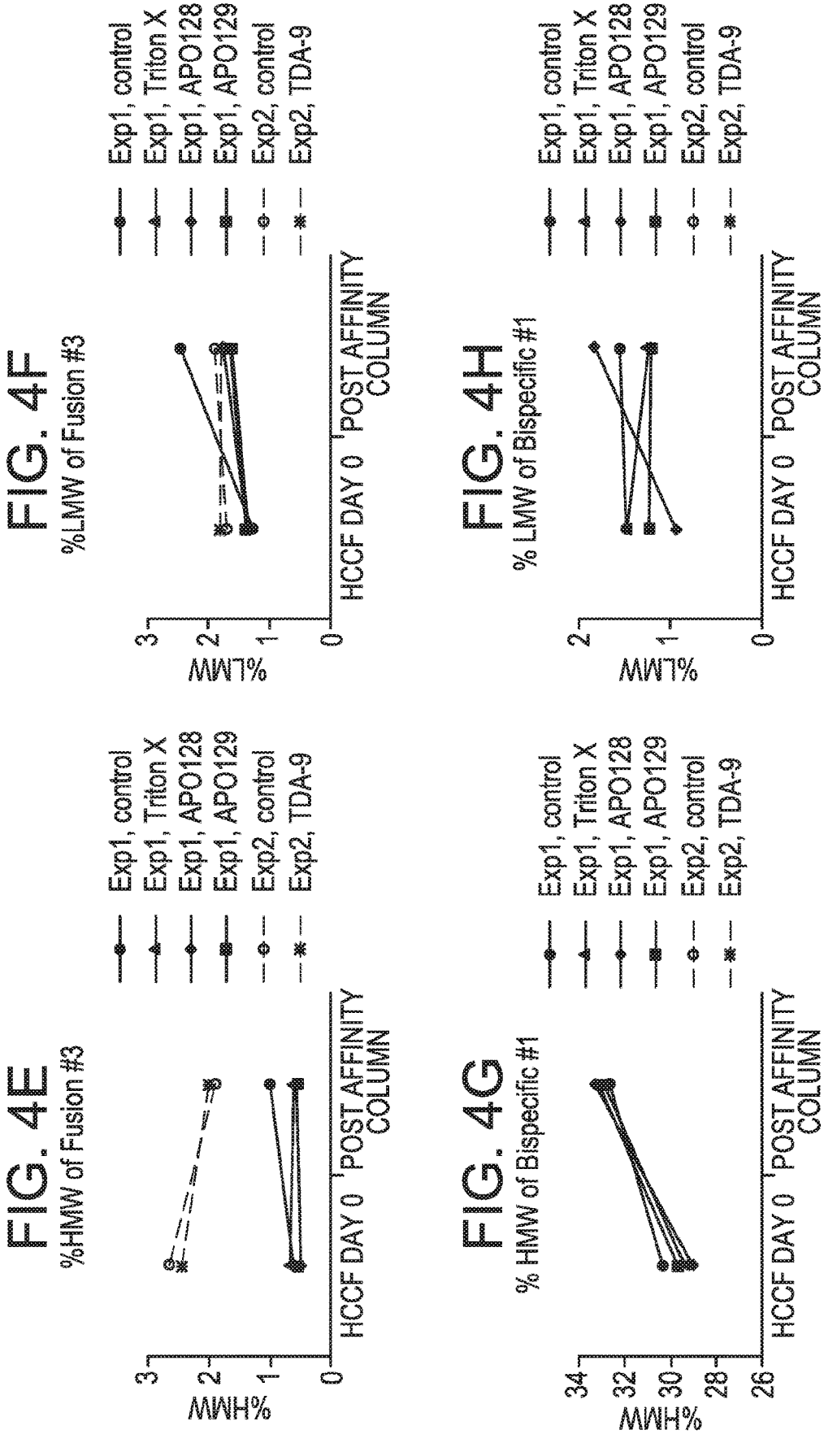
FIG. 4: % HMW and % LMW for detergent spiked samples before and after affinity chromatography. Triton X, triangle; Anapoe C12E8 (APO128), diamond; Anapoe C12E8 (APO129), square; no detergent control, circle; TDA-9 dashed line and star; second no detergent control, dashed line, open circle.

FIG. 4 shows the stability of molecules across the affinity capture process as measured by % HMW and % LMW. The data was normalized by subtracting the value of the no detergent control. For most of the molecules, the % HMW and % LMW stayed constant before and after affinity capture step. BiTE #2 was known to be unstable at the post-affinity chromatography pool stage, hence the wide variation in % HMW.

Figures 5A, 5B:
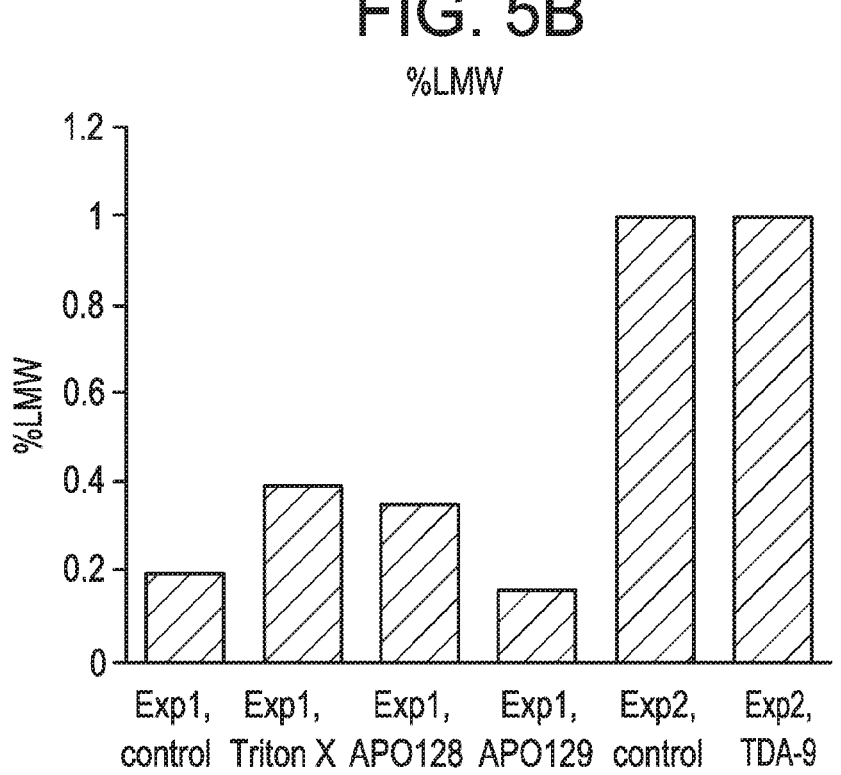
FIG. 5: % HMW and % LMW for detergent spiked BiTE® #1 samples before and after affinity chromatography.

FIG. 5 shows the product quality data for BiTE #1 after the affinity. BiTE #1 HCCF (the load material) was not submitted for product quality prior to the affinity chromatography.

Figures 6E, 6F, 6G, 6H:
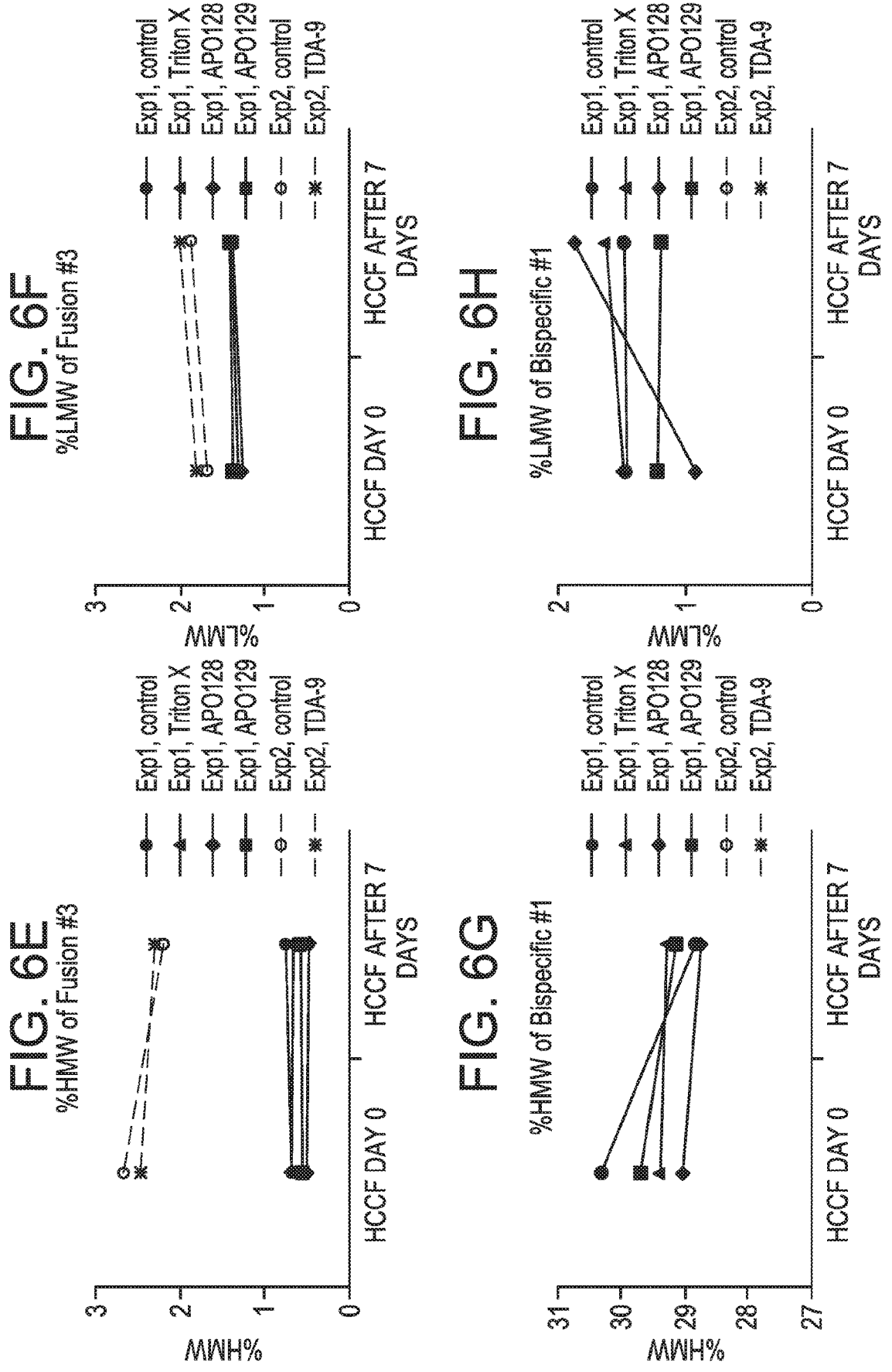
FIG. 6: % HMW and % LMW in detergent spiked HCCF samples following a seven-day incubation at 2-8° C. Triton X, triangle; Anapoe C12E8 (APO128), diamond; Anapoe C12E8 (APO129), square; no detergent control, circle; no detergent control, circle; TDA-9 dashed line and star; second no detergent control, dashed line, open circle.
Figures 6I, 6J:
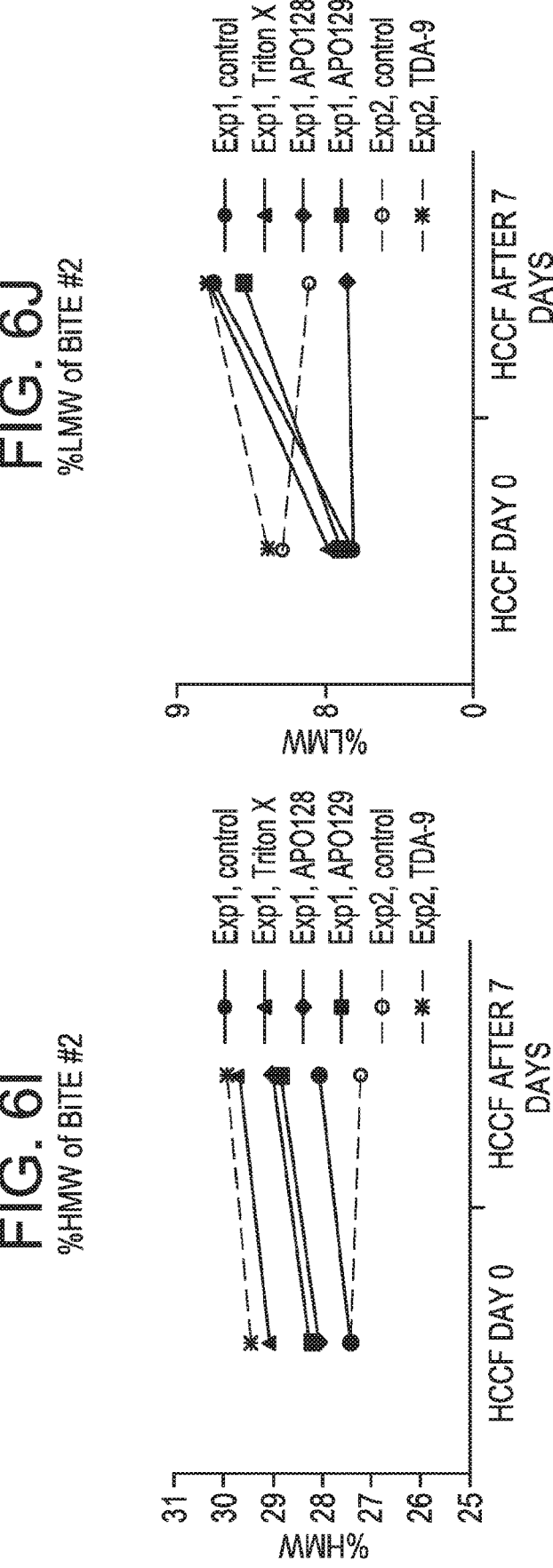

FIG. 6 shows the stability of the molecules stayed relatively constant after 7 days incubation at 2-8° C. as measured by % HMW and % LMW. The data was normalized by subtracting the value of the no detergent control.

The detergents had no significant impact on product quality during affinity chromatography.

What is claimed is:

1. A method for inactivating envelope virus in a fluid known or suspected to contain at least one enveloped virus, comprising obtaining a fluid known or suspected to contain at least one enveloped virus;

exposing the fluid to a detergent having a CAS registry number of CAS 3055-99-0, CAS 9043-30-5, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 82494-09-5, CAS 253678-67-0, CAS 106402-05-5, or CAS 93911-12-7;

at a detergent concentration that is 2.5× to 10× of its Critical Micelle Concentration (CMC) and time sufficient to cause viral inactivation.

2. The method according to claim 1 wherein the fluid is exposed to the detergent for at least 30 seconds to at least 60 minutes or longer.

3. The method according to claim 2 wherein the fluid is exposed to the detergent for at least 10 minutes.

4. The method according to claim 1, wherein the detergent concentration is at least 5× of its CMC.

5. The method according to claim 1, wherein exposure of the fluid to the detergent occurs at a temperature of at least 5° C. to 22° C.

6. The method according to claim 5, wherein exposure of the fluid to the detergent occurs at a temperature of at least 15° C.

7. The method according to claim 1, wherein the detergent concentration is 5× of its CMC and the time is at least 10 minutes.

8. The method according to claim 1, wherein the fluid comprises a recombinant protein of interest.

9. The method according to claim 1, wherein the fluid is harvested host cell culture fluid.

10. The method according to claim 1, wherein the fluid is from an effluent stream, eluate, pool, storage or hold from a unit operation comprising a harvest step, a filtration step or a chromatography step.

11. The method according to claim 10, wherein the fluid is (i) eluate collected from depth filtration, microfiltration, affinity chromatography, ion exchange chromatography, multimodal chromatography, hydrophobic interaction chromatography or hydroxyapatite chromatography; or (ii) a pool containing harvested cell culture fluid, eluate from depth filtration, eluate from microfiltration, eluate from affinity chromatography, eluate from ion exchange chromatography, eluate from multimodal chromatography, eluate from hydrophobic interaction chromatography, or eluate from hydroxyapatite chromatography.

12. The method according to claim 11, wherein the affinity chromatography is Protein A, Protein G, Protein A/G, or Protein L chromatography.

13. A method for inactivating enveloped viruses during purification of a recombinant protein of interest comprising obtaining a fluid comprising the recombinant protein of interest which is known or suspected to contain at least one virus;

subjecting the fluid to at least one detergent, wherein the detergent has a CAS registry number of CAS 3055-99-0, CAS 9043-30-5, CAS 181135-58-0, CAS 181135-57-9, CAS 250692-65-0, CAS 228579-27-9, CAS 349477-49-2, CAS 70504-28-8, CAS 59080-45-4, CAS 69984-73-2, CAS 148616-91-5, CAS 148565-55-3, CAS 82494-09-5, CAS 253678-67-0, CAS 106402-05-5, or CAS 93911 12-7 at a detergent concentration that is 5× of its Critical Micelle Concentration (CMC) and for at least 10 minutes to cause inactivation of enveloped viruses in the fluid; and subjecting the viral inactivated fluid to at least one unit operation which includes at least a filtration step or a chromatography step.

14. The method according to claim 13, wherein the chromatography is selected from affinity chromatography, Protein A chromatography, ion exchange chromatography, anion exchange chromatography, cation exchange chromatography; hydrophobic interaction chromatography; mixed modal or multimodal chromatography, or hydroxyapatite chromatography.

15. The method according to claim 13, wherein:

(i) the fluid is harvested host cell culture fluid and the unit operation includes depth filtration;

(ii) the fluid is harvested host cell culture fluid and the unit operation includes microfiltration;

(iii) the fluid is harvested host cell culture fluid and the unit operation includes Protein A affinity chromatography; or (iv) the fluid is Protein A eluant and the unit operation includes depth filtration.

16. The method according to claim 13, wherein the unit operation includes depth filtration or microfiltration.

17. The method of claim 1, wherein the detergent has a CAS registry number of CAS 3055-99-0 or CAS 9043-30-5.

18. The method of claim 13, wherein the detergent has a CAS registry number of CAS 3055-99-0 or CAS 9043-30-5.

19. The method of claim 17, wherein the detergent has a CAS registry number of CAS 3055-99-0.

20. The method of claim 17, wherein the detergent has a CAS registry number of CAS 9043-30-5.

21. The method of claim 18, wherein the detergent has a CAS registry number of CAS 3055-99-0.

22. The method of claim 18, wherein the detergent has a CAS registry number of CAS 9043-30-5.

23. A method for inactivating envelope virus in a fluid known or suspected to contain at least one enveloped virus, comprising obtaining a fluid known or suspected to contain at least one enveloped virus;

exposing the fluid to a detergent which is TDA-9, at a detergent concentration that is 2.5X to 10X of its Critical Micelle Concentration (CMC) and time sufficient to cause viral inactivation.

* * * * *